US006521427B1

(12) United States Patent
Evans

(10) Patent No.: US 6,521,427 B1
(45) Date of Patent: Feb. 18, 2003

(54) METHOD FOR THE COMPLETE CHEMICAL SYNTHESIS AND ASSEMBLY OF GENES AND GENOMES

(75) Inventor: Glen A. Evans, San Marcos, CA (US)

(73) Assignee: Egea Biosciences, Inc., San Diego, CA (US)

( * ) Notice: Subject to any disclaimer, the term of this patent is extended or adjusted under 35 U.S.C. 154(b) by 0 days.

(21) Appl. No.: 09/554,929

(22) PCT Filed: Sep. 16, 1998

(86) PCT No.: PCT/US98/19312

§ 371 (c)(1),
(2), (4) Date: May 12, 2000

(87) PCT Pub. No.: WO99/14318

PCT Pub. Date: Mar. 25, 1999

Related U.S. Application Data

(60) Provisional application No. 60/059,017, filed on Sep. 16, 1997.

(51) Int. Cl.[7] .......................... C12P 19/34; C12Q 1/68; C07H 21/02; A01N 35/00; C12N 15/00
(52) U.S. Cl. ..................... 435/91.1; 435/6; 435/91.4; 536/23.1; 536/24.2; 514/675; 514/690; 800/25; 800/205
(58) Field of Search .............................. 435/6, 66, 91.1, 435/91.4, 194; 536/23.1, 24.2, 24.3, 24.31; 514/675, 690; 424/93.2; 800/25, 205

(56) References Cited

U.S. PATENT DOCUMENTS

| | | | |
|---|---|---|---|
| 4,652,639 A | | 3/1987 | Stabinsky ..................... 536/27 |
| 5,096,825 A | * | 3/1992 | Barr et al. ................... 435/255 |
| 5,198,346 A | | 3/1993 | Ladner et al. ............. 435/69.1 |
| 5,387,756 A | * | 2/1995 | Burrell et al. ............... 800/205 |
| 5,922,927 A | * | 7/1999 | Bujard et al. ................. 800/205 |
| 5,925,538 A | * | 7/1999 | Perkins et al. ................. 435/66 |
| 5,968,799 A | * | 10/1999 | Gelfand et al. ............. 435/194 |
| 5,981,601 A | * | 11/1999 | Nagley et al. .............. 514/690 |
| 6,087,100 A | * | 7/2000 | Meade et al. ................... 435/6 |
| 6,110,457 A | * | 8/2000 | Belshe et al. ............. 424/93.2 |

FOREIGN PATENT DOCUMENTS

| | | |
|---|---|---|
| EP | 0 316 018 | 2/1986 |
| EP | 0 385 410 | 2/1990 |
| WO | WO9000626 | 1/1990 |
| WO | WO9412632 | 6/1994 |

OTHER PUBLICATIONS

Beattie, K.L., et al., Gene Synthesis Technology: Recent Developments and Future Prospects, Biotechnology and Applied Biochemistry 10, pp. 510–521 (1988).*
Sulo et al., "Isolation and Characterization of LIP5", *The Journal of Biological Chemistry*, vol. 268 (23), pp. 17634–17639, Mar. 1993.*

Edge et al., "Total Synthesis of a human leukocyte interferon gene", Nature, vol. 292, pp. 756–762, Aug. 1981.*
Agarwal et al., "Synthesis, cloning and expression of a synthetic gene for high potential iron protein from *chromatium vinosum*," *Biochem. Biophys. Res. Commun.*, 197(3):1357–1362 (1993).
Ashman et al., "Chemical synthesis, expression and product assessment of a gene coding for biologically active human tumor necrosis factor alpha," *Protein Eng.*, 2(5):387–391 (1989).
Bell et al., "Chemical synthesis cloning and expression in mammalian cells of a gene coding for human tissue–type plasminogenactivator" *Gene*, 63:155–163 (1988).
Bergmann et al., "Chemical synthesis and expression of a gene coding for hirudin, the thrombin–specific inhibitor from the leech *hirudo medicinalis*," *Biol. Chem. Hoppe. Seyler.*, 367(8):731–740 (1968).
Biernat et al., "The construction and cloning of synthetic genes coding for artificial proteins and expression studies to obtain fusion proteins," *Protein Eng.*, 1(4):345–351 (1987).
Calogero et al., "Chemical synthesis and in vivo hyperexpression of a modular gene coding for *Escherichia coli* translational initiation factor IF1," *Mol. Gen. Genet.*, 208:63–69 (1987).
Ciccarelli et al., "Construction of synthetic genes using PCR after automated DNA synthesis of their entire top and bottom strands," *Nucleic Acids. Res.*, 19(21):6007–6013 (1991).
Cravador et al., "Total DNA synthesis and cloning in *Escherichia coli* of a gene coding for the human growth hormone releasing factor," *Biochimie.*, 67:829–834 (1985).
Danilyuk et al., "Effective synthesis and cloning of the gene of human interleukin–2 gene and an analog of it: expression of the interleukin–2 gene in *E. coli* cells," *Bioorg. Chem.*, 17(6):446–454 (1991).
Denéfle et al., "Chemical synthesis of a gene coding for human angiogenin, its expression in *Escherichia coli* and conversion of the product into its active form," *Gene*, 56:61–70 (1987).

(List continued on next page.)

*Primary Examiner*—W. Gary Jones
*Assistant Examiner*—Arun K. Chakrabarti
(74) *Attorney, Agent, or Firm*—Campbell & Flores LLP

(57) ABSTRACT

The present invention relates generally to the fields of oligonucleotide synthesis. More particularly, it concerns the assembly of genes and genomes of completely synthetic artificial organisms. Thus, the present invention outlines a novel approach to utilizing the results of genomic sequence information by computer directed gene synthesis based on computing on the human genome database. Specifically, the present invention contemplates and describes the chemical synthesis and resynthesis of genes defined by the genome sequence in a host vector and transfer and expression of these sequences into suitable hosts.

45 Claims, 21 Drawing Sheets

OTHER PUBLICATIONS

Dillon et al., "A rapid method for the construction of synthetic genes using the polymerase chain reaction," *Biotechniques*, 9(3):298–300 (1990).

Dobrynin et al., "Chemical–enzymatic synthesis and cloning of DNA, coding the signal for secretion of proteins in gram–negative bacteria," *Bioorg. Chem.*, 15(9):684–690 (1989).

Dobrynin, et al., "Synthesis of a model promoter for a gene expression in *Escherichia coli*," *Nucleic Acids Symp. Ser.*, 7:365–376 (1980).

Edge et al., "Total synthesis of a human leukocyte interferon gene," *Nature*, 292:756–762 (1981).

Eidsness et al., "Expression of a synthetic gene coding for the amino acid sequence of *clostridium pasteurianum* rubredoxin," *Protein Eng.*, 5(4):367–371 (1992).

Eren and Swenson, "Chemical synthesis and expression of a synthetic gene for the flavodoxin from clostridium MP," *J. Biol. Chem.*, 264(25)14874–14879 (1989).

Farrow et al., "Synthesis of a gene for the protein kinase domain of the epidermal growth factor receptor and its expression in *Escherichia coli*," *Eur. J. Biochem.*, 184:361–365 (1989).

Ferretti, et al., "Total synthesis of a gene for bovine rhodopsin," *Proc. Natl. Acad. Sci. USA*, 83:599–603 (1986).

Foguet and Lubbert "Precise and efficient construction of synthetic genes," *Biotechniques*, 13(5):674–675 (1992).

Gearing et al., "Chemical synthesis of a mitochondrial gene designed for expression in the yeast nucleus," *Biochem. Int.*, 10(6):907–915 (1985).

Gurevich et al., "Chemical–enzymatic synthesis of the translation–enhancer gene 10 of phage T7 and function of elements of its structure," *Bioorg. Chem.*, 17(5):371–376 (1991).

Gurevich et al, "Construction of artificial genes by PCR methods using the synthetic template," *Bioorg. Khim.*, 23(6):492–496 (1997).

Harada et al., "Total synthesis of a gene for octopus rhodopsin and its preliminary expression," *J. Biochem.*, 110:501–507 (1991).

Henze et al., "Expression of the chemically synthesized coding region for the cytotoxin alpha–sarcin in *Escherichia coli* using a secretion cloning vector," *Eur J. Biochem.*, 192(1):127–131 (1990).

Hostomskÿ et al., "Solid–phase assembly of cow colostrum trypsin inhibitor gene," *Nucleic Acid Research*, 15(12):4849–4855 (1987).

Ikehara et al., "Synthesis of a gene for human growth hormone and its expression in *Escherichia coli*," *Proc. Natl. Acad, Sci. USA*, 81(19):5956–5960 (1984).

Inaoka et al., "Chemical synthesis of the T4 endonucleases V gene and its expression in *Escherichia coli*." *Nucleic Acids Symp. Ser.*, 17:105–108 (1986).

Kaji et al., "Studies on chemical synthesis of human cystatin a gene and its expression in *Escherichia coli*," *J. Biochem (Tokyo)*, 105(1):143–147 (1989).

Kálmán et al., "Synthesis of a gene for human serum albumin and its expression in *saccharomyces cerevisiae*," *Nucleic Acids Res.*, 18(20):6075–6081 (1990).

Kaltenboek and Kousoulas "Efficient PCR production of a single–stranded DNA sequencing templates," *Methods Mol. Biol.*, 65:149–153 (1996).

Kash'yap et al., "Chemical–enzymatic synthesis and cloning in *Escherichia coli* of the gene coding human granulocyte–colony–stimulating factor," *Bioorg. Chem.*, 18(1):18–22 (1992).

Katunuma et al., "Total synthesis of the cystatin alpha gene and its expression in *E. coli*," *FEBS Lett.*, 238(1):116–118 (1988).

Kim et al., "Chemical synthesis and cloning of human beta–endorphin gene in *Escherichia coli*," *Appl. Biochem Biotechnol.*, 50(1):35–43 (1995).

Lashkari et al., "An automated multiplex oligonucleotide synthesizer: development of high throughput, low–cost DNA synthesis" *Proc. Natl. Acad. Sci. USA*, 92(17):7912–7915 (1995).

Lebedenko et al., "Synthesis and modification of genes through artificial splicing by directed ligation (ASDL)," *Nucleic Acids Symp. Ser.*, 24:215–216 (1991).

Lebedenko et al., "Method of artificial DNA splicing by directed ligation (SDL)," *Nucleic Acids. Res.*, 19(24):6757–6761 (1991).

Modesti, et al., "Chemical synthesis and expression of a gene coding for human muscle acylphophatase," *Biochim. Biophys. Acta.*, 1216(3):369–374 (1993).

Nagase et al. "Chemical synthesis of a human fibroblast interferon gene and its expression in *Escherichia coli*," *Nucleic Acids Symp. Ser.*, 12:83–86 (1983).

Prodromou and Pearl, "Recursive PCR: a novel technique for total gene synthesis," *Protein Eng.*, 5(8):827–829 (1992).

Rayner et al., "MerMade: an oligodeoxyribonucleotide synthesizer for high throughput oligonucleotide production in dual 96–well plates" *Genome Research*, 8(7):741–747 (1998).

Roberts et al., "Chemical synthesis and expression of a calmodulin gene designed for site–specific mutagenesis," *Biochemistry*, 24(19):5090–5098 (1985).

Rosenthal et al. "Chemical–enzymatic synthesis, cloning and expression of a synthetic gene coding for an env protein fragment of the human T–cell leukemia virus type 1," *Nucleic Acids Sump. Ser.*, 18:233–236 (1987).

Sandhu et al., "Dual asymmetric PCR: one–step construction of synthetic genes," *Biotechniques*, 12(1):14–16 (1992).

Sindelar and Jaklevic, "High–throughput DNA synthesis in a multichannel format" *Nucleic Acid Res.*, 23(6):982–987 (1995).

Strauss et al., "Chemical synthesis of a gene for human stefin A and its expression in *E. coli*," *Biol. Chem. Hoppe Seyler*, 369(9):1019–1030 (1988).

Strauss et al., "Chemical synthesis of a gene for human cystatin C and its expression in *E. Coli*," *Biol. Chem. Hoppe Seyler*, 369:209–218 (1988).

Sulo and Martin, "Isolation and characterization of LIP5," *J. Biol. Chem.*, 268(23):17634–17639 (1993).

Suwen et al., "Chemical synthesis and cloning of secretin gene," *Sci. Sin [B]*, 31(6):687–694 (1988).

Tanaka et al., "Expression in *Escherichia coli* of chemically synthesized gene for a human immune interferon," *Nucleic Acids Symp. Ser.*, 11:29–32 (1982).

Thompson and Weber, "Construction and expression of a synthetic streptavidin–encoding gene in *Escherichia coli*," *Gene*, 136(1–2):243–246 (1993).

Wosnick et al., "Total chemical synthesis and expression in *Escherichia coli* of a maize glutathione–transferase (GTS) gene," *Gene*, 76:153–160 (1989).

\* cited by examiner

Step 1. Determine/design DNA sequence of the genome

Step 2. Synthesize and assemble the genomic DNA

Step 3. Introduce the DNA into an enucleated pleuripotent host cell.

Step 4. Introduce the host cell into a foster mother animal

SYNTHETIC ORGANISM

FIG. 1

1. Design genome, containing prokaryotic origin of replication and drug selection vector.

2. SynGen 2.0, breaks down genome into component overlapping oligonucleotides, programs oligonucleotide synthesizer.

3. Chemcial synthesis of component oligonucleotide using MERMADE high throughput synthesizer.

4. Combinatoric assembly of component oligonucleotides using robotic processing.

5. Transformation into component bacteria.

FIG. 2

```
           10              20              30              40              50              60              70              80              90              100
aagcttacctcgatttgaggacgttacaagtattactgttaaggagcgtagattaaaaatgaaatgaattattagaattggcttaaataac
agaatcaccaaaaagaatagagtagagtttgaagtttggaaatatttgttttcgtatcaaccaccagtgaaactcataagctaagtaatggatcgcttttgtt
                 luxA --- >
cggcttggtatcgcctcagaagagtagggtttgatacatattggacctttagaacatcatttacagagtttgtcttacgggaaatttatttgttgctgc
ggctaacctgttaggaagaactaaaacattaaatgttggcactatgttgtattccgacagcacaccagttcgacagttagaagacgttttatta
ttagatcaaatgtcgaaagtgctgttttaattttggaaccgttcgagggctataccataaagatttcgagtatttggtgtgtatggaagagtctcgag
caattactcaaaatttctaccagatgataatgaaaagttctactagttacgacagacaggaacttacgacagaaccattagctctgatagtgattacattcattcctaaggttgatgtata
tcccaaagtgtactcaaaaatgtaccaacctgtatgactgctgagtccgcaagtacgacagaatggctagcaatacaagggctaccaatggttcttagt
tggattattggtactaatgaaaaaagcacagatgaactctataatgaaatgcagacagaataggtcatgatatatctaaaatagatcattgatga
cttatatttgtctgttgatgatgagcagaatctgtggttatcataaagtcaatgcgtgtatttacaaggacatacaaccatcgacgtgtgat
ctttaatgatagcaatcaactctgtgttattcatcctgagcagtgattgaaatcattcaacgtgattatgatcaacgaagtattacaaacattacatgcggat
tatgcaatggtattaccctgtaggctccgtaggatgaaataattgcttccatgcgacgcttttatgacgacgttcctaaagaccttatcttctaaacttatttt
ttgaagctaatgaactgaagatgaaacaagttatgaaatttgaatttttttctcaaactttcagaaagatgaataacatctgaagaacgttgataaatatgg
gatactagagataataaggaacagttatgaaattatgaaattttatctgaaatatttatctgattaataagatgagaattcactgccg
                 luxB --- >
taaagactgtcacgttaattgattcaactaaatatcatttaatactgccttgttaatgaacatcacttttcaaaaaatgtattgttggagcacctat
taccgcagtcgttgtttttattggttaacaaatacatattggttcattaaatcaagtaattaccacccatccctgtacgtgtacgcagagaa
gccagttatgaaaatcaaatgtcaggagggacgcttcattcttggttgtactacagttgatttcgaaatggaatttttagacgtcatatctcat
caaggcaacaacattgaagcatgtatgaaatataatgacgcattaactacacagttattgtcatcccaaaacgacttttatgatttccaaagt
ttcaattaatccacactgttacagtgagaatgacctaagacgaactagagagctactacaaaagatatcgctacatgtactcatcaaaagaagtgtcatgtgggcagcgaaaagaggcactgcct
taacatttaagtgggagataattagaaccaaagaacgctatgcaattctcttatataaaaaacgcacaacatgtattgatatttcgatgttg
atcatcaattaactgtaattgcgaacttaaactatatccttatatagatattttatctgaaatattttatctgattaataagatgagaattcactggatgtg
tcaaatgacagagatgaaaatattttaaggctgataagagtacggctcaagaagtcagttgctcatgatgactattatgaatcgacaaattagcagtggaaaa
acagggtctaaaataaaattaactcttttaaagatgtccgatattaaagatgtaacaaaatgaatgaattt
taccataataaaattaaggcaatttctatattagattgcctttgggatcctctagaatatttatctgaaatatttatctgattaataagatgagaattcactggccg
                 pUC 19 --- >
```

FIG. 4A tcgtttacaacgtcgtgactgggaaacccctggcgttaccccaactttaatcgccttgcagcacatcccctttcgccagtggcgtaatagcgaagaggc
ccgcaccgatcgcccttcccaacagttgcgcagcctgaatggcgaatggcgcctgatgcggtattttctccttacgcatctgtgcggtatttcacaccgc
atatggtgcactctcagtacaatctgctctgatgccgcatagttaagcagccgcacacccgctgacgcgccctgacggcttgtctgc
tcccggcatccgcttacagacaagctgtgaccggcgtctccgggagctgcatgtgtcagaggttttcaccgtcatcaccgaaacgcgcgagacgaaagggcct
cgtgatacgcctattttatagttcatgtcatgataataatggtttcttagacgtcaggtggcactttcggggaaatgtgcgcggaacccctatttgt
ttattttctaaaaagcttcacgctgccgcaagcactcaggcgcaagctgctagaacgaacagcgaacgaacagcagtagagaaagcagtccgagaaacggtgct
gacccgatgaatgtcagctactggctatctgacaagaaacgaaccgaaattgcagctgggcgcctctgtaagttgggaagcccctgtaagttggagcccctgtaaccct
agactgggcggttttatgacagcaagcaaccggaattgcagctggcgggcttgcgaagaaccggaaatccctgtaagttgggaagcccctgtaagttggagctaccgctcgatagct
ttgccgccaaggatctgatgcgcaggcgcaggtcaagatctgatcaagagacacaggatcaagagatgaggatcgttcgatgattgaacaagatgattgcacgcaggtt
----- kan/neo phosphotransferase -----
ctccggccgcttgggtggagaggctattcggctatgactgggcacaacagacaatcgtctgtctgatgccgccgtgttccggctgtcagcgcaggggcg
---->
cccggttcttttttgtcaagaccgacctgtccggtgccctgaatgaactgcaggacgaggcagcgcggctatcgtggctggccacgacgggcgttccttgc
gcagctgtgctcgacgttgtcactgaagcggggaaggactggctgctattgggcgaagtgccggggcaggatctcctgtcatctcaccttgctcctgccg
agaaagtatccatcatggctgatgcaatgcggcggctgcatacgcttgatccggctacctgcccattcgaccaccaagcgaaacatcgcatcgagcgagc
acgtactcggatggaagccggtcttgtcgatcaggatgatctggacgaagagcatcagggggctcgcgccagccgaactgttcgccaggctcaaggcgc
atgcccgacggcgaggatctcgtcgtgacccatggcgatgcctgcttgccgaatatcatggtggaaaatggccgcttttctggattcatcgactgtggcc
ggctgggtgtggcggaccgctatcaggacatagcgttggctacccgtgatattgctgaagagcttggcggcgaatgggctgaccgcttcctcgtgctttta
cggtatcgccgctcccgattcgcagcgcatcgccttctatcgccttcttgacgagttcttctgagcgggactctgggttcgaaatgaccgaccaagcga
cgcccaacctgccatcacgagatttcgattccaccgccgccttctatgaaaggttgggcttcggaatcgttttccggacgccggctgatgatcctcca
pUC19 ---->

FIG. 4B

```
gcgcgggatcctcatgctggagttcttcgcccaccccgggcatgaccaaatcccttaacgtgagttttcgttccactgagcgtcagaccccgtagaaaa
gatcaaggatcctttgagatcctttttctgcgctaatctgctgttgcaaacaaaaaaccaccgctaccagcggtggtttgtttgccgatcaa
gagctaccaactcttttccgaagtaactggcttcagcagcgcagataccaaatactgtccttctagtgtagccgtagttaggccaccacttcaaga
actctgtagcaccgcctacatacctcgctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcgaacgacctacaccgaactgagatacctacag
cgtgagctatgagaaagcgccacgcttcccgaagggagaaaggcggacaggtatccggtaagcggcagggtcggaacaggagagcgcacgagggagcttc
caggggggaaacgcctggtatctttatagtcctgtcgggtttcgccacctctgacttgagcgtcgatttttgtgatgctcgtcaggggggcggagcctatg
```

FIG. 4C

```
oligoF01,AAGCTTACCTCGATTTGAGGACGTTACAAGTATTACTGTTAAGGAGCGTA
oligoF02,GATTAAAAAATGAAATTGAAAATGAATTATTAGAATTGGCTTAAATAAAC
oligoF03,AGAATCACCAAAAAGGAATAGAGTATGAAGTTTGGAAATATTTGTTTTTC
oligoF04,GTATCAACCACCAGGTGAAACTCATAAGCTAAGTAATGGATCGCTTTGTT
oligoF05,CGGCTTGGTATCGCCTCAGAAGAGTAGGGTTTGATACATATTGGACCTTA
oligoF06,GAACATCATTTTACAGAGTTTGGTCTTACGGGAAATTTATTTGTTGCTGC
oligoF07,GGCTAACCTGTTAGGAAGAACTAAAACATTAAATGTTGGCACTATGGGGG
oligoF08,TTGTTATTCCGACAGCACACCCAGTTCGACAGTTAGAAGACGTTTTATTA
oligoF09,TTAGATCAAATGTCGAAAGGTCGTTTTAATTTTGGAACCGTTCGAGGGCT
oligoF10,ATACCATAAAGATTTTCGAGTATTTGGTGTTGATATGGAAGAGTCTCGAG
oligoF11,CAATTACTCAAAATTTCTACCAGATGATAATGGAAAGCTTACAGACAGGA
oligoF12,ACCATTAGCTCTGATAGTGATTACATTCAATTTCCTAAGGTTGATGTATA
oligoF13,TCCCAAAGTGTACTCAAAAAATGTACCAACCTGTATGACTGCTGAGTCCG
oligoF14,CAAGTACGACAGAATGGCTAGCAATACAAGGGCTACCAATGGTTCTTAGT
oligoF15,TGGATTATTGGTACTAATGAAAAAAAAGCACAGATGGAACTCTATAATGA
oligoF16,AATTGCGACAGAATATGGTCATGATATATCTAAAATAGATCATTGTATGA
oligoF17,CTTATATTTGTTCTGTTGATGATGATGCACAAAAGGCGCAAGATGTTTGT
oligoF18,CGGGAGTTTCTGAAAAATTGGTATGACTCATATGTAAATGCGACCAATAT
oligoF19,CTTTAATGATAGCAATCAAACTCGTGGTTATGATTATCATAAAGGTCAAT
oligoF20,GGCGTGATTTTGTTTTACAAGGACATACAAACACCAATCGACGTGTTGAT
oligoF21,TATAGCAATGGTATTAACCCTGTAGGCACTCCTGAGCAGTGTATTGAAAT
oligoF22,CATTCAACGTGATATTGATGCAACGGGTATTACAAACATTACATGCGGAT
oligoF23,TTGAAGCTAATGGAACTGAAGATGAAATAATTGCTTCCATGCGACGCTTT
oligoF24,ATGACACAAGTCGCTCCTTTCTTAAAAGAACCTAAATAAATTACTTATTT
oligoF25,GATACTAGAGATAATAAGGAACAAGTTATGAAATTTGGATTATTTTTTCT
oligoF26,AAACTTTCAGAAAGATGGAATAACATCTGAAGAAACGTTGGATAATATGG
oligoF27,TAAAGACTGTCACGTTAATTGATTCAACTAAATATCATTTTAATACTGCC
oligoF28,TTTGTTAATGAACATCACTTTTCAAAAAATGGTATTGTTGGAGCACCTAT
oligoF29,TACCGCAGCTGGTTTTTTATTAGGGTTAACAAATAAATTACATATTGGTT
```

FIG. 5A oligoF30,CATTAAATCAAGTAATTACCACCCATCACCCTGTACGTGTAGCAGAAGAA
oligoF31,GCCAGTTTATTAGATCAAATGTCAGAGGGACGCTTCATTCTTGGTTTTAG
oligoF32,TGACTGCGAAAGTGATTTCGAAATGGAATTTTTTAGACGTCATATCTCATV
oligoF33,CAAGGCAACAACAATTTGAAGCATGCTATGAAATAATTAATGACGCATTA
oligoF34,ACTACAGGTTATTGTCATCCCCAAAACGACTTTTATGATTTTCCAAAGGT
oligoF35,TTCAATTAATCCACACTGTTACAGTGAGAATGGACCTAAGCAATATGTAT
oligoF36,CCGCTACATCAAAAGAAGTCGTCATGTGGGCAGCGAAAAAGGCACTGCCT
oligoF37,TTAACATTTAAGTGGGAGGATAATTTAGAAACCAAAGAACGCTATGCAAT
oligoF38,TCTATATAATAAAACAGCACAACAATATGGTATTGATATTTCGGATGTTG
oligoF39,ATCATCAATTAACTGTAATTGCGAACTTAAATGCTGATAGAAGTACGGCT
oligoF40,CAAGAAGAAGTGAGAGAATACTTAAAAGACTATATCACTGAAACTTACCC
oligoF41,TCAAATGGACAGAGATGAAAAAATTAACTGCATTATTGAAGAGAATGCAG
oligoF42,TTGGGTCTCATGATGACTATTATGAATCGACAAAATTAGCAGTGGAAAAA
oligoF43,ACAGGGTCTAAAAATATTTTATTATCCTTTGAATCAATGTCCGATATTAA
oligoF44,AGATGTAAAAGATATTATTGATATGTTGAACCAAAAAATCGAAATGAATT
oligoF45,TACCATAATAAAATTAAAGGCAATTTCTATATTAGATTGCCTTTTTGGGG
oligoF46,ATCCTCTAGAAATATTTTATCTGATTAATAAGATGAGAATTCACTGGCCG
oligoF47,TCGTTTTACAACGTCGTGACTGGGAAAACCCTGGCGTTACCCAACTTAAT
oligoF48,CGCCTTGCAGCACATCCCCCTTTCGCCAGCTGGCGTAATAGCGAAGAGGC
oligoF49,CCGCACCGATCGCCCTTCCCAACAGTTGCGCAGCCTGAATGGCGAATGGC
oligoF50,GCCTGATGCGGTATTTTCTCCTTACGCATCTGTGCGGTATTTCACACCGC
oligoF51,ATATGGTGCACTCTCAGTACAATCTGCTCTGATGCCGCATAGTTAAGCCA
oligoF52,GCCCCGACACCCGCCAACACCCGCTGACGCGCCCTGACGGGCTTGTCTGC
oligoF53,TCCCGGCATCCGCTTACAGACAAGCTGTGACCGTCTCCGGGAGCTGCATG
oligoF54,TGTCAGAGGTTTTCACCGTCATCACCGAAACGCGCGAGACGAAAGGGCCT
oligoF55,CGTGATACGCCTATTTTTATAGGTTAATGTCATGATAATAATGGTTTCTT
oligoF56,AGACGTCAGGTGGCACTTTTCGGGGAAATGTGCGCGGAACCCCTATTTGT
oligoF57,TTATTTTTCTAAAAAGCTTCACGCTGCCGCAAGCACTCAGGGCGCAAGGG
oligoF58,CTGCTAAAGGAAGCGGAACACGTAGAAAGCCAGTCCGCAGAAACGGTGCT
oligoF59,GACCCCGGATGAATGTCAGCTACTGGGCTATCTGGACAAGGGAAAACGCA
oligoF60,AGCGCAAAGAGAAAGCAGGTAGCTTGCAGTGGGCTTACATGGCGATAGCT
oligoF61,AGACTGGGCGGTTTTATGGACAGCAAGCGAACCGGAATTGCCAGCTGGGG

FIG. 5B oligoF63,TTGCCGCCAAGGATCTGATGGCGCAGGGGATCAAGATCTGATCAAGAGAC
oligoF64,AGGATGAGGATCGTTTCGCATGATTGAACAAGATGGATTGCACGCAGGTT
oligoF65,CTCCGGCCGCTTGGGTGGAGAGGCTATTCGGCTATGACTGGGCACAACAG
oligoF66,ACAATCGGCTGCTCTGATGCCGCCGTGTTCCGGCTGTCAGCGCAGGGGCG
oligoF67,CCCGGTTCTTTTTGTCAAGACCGACCTGTCCGGTGCCCTGAATGAACTGC
oligoF68,AGGACGAGGCAGCGCGGCTATCGTGGCTGGCCACGACGGGCGTTCCTTGC
oligoF69,GCAGCTGTGCTCGACGTTGTCACTGAAGCGGGAAGGGACTGGCTGCTATT
oligoF70,GGGCGAAGTGCCGGGGCAGGATCTCCTGTCATCTCACCTTGCTCCTGCCG
oligoF71,AGAAAGTATCCATCATGGCTGATGCAATGCGGCGGCTGCATACGCTTGAT
oligoF72,CCGGCTACCTGCCCATTCGACCACCAAGCGAAACATCGCATCGAGCGAGC
oligoF73,ACGTACTCGGATGGAAGCCGGTCTTGTCGATCAGGATGATCTGGACGAAG
oligoF74,AGCATCAGGGGCTCGCGCCAGCCGAACTGTTCGCCAGGCTCAAGGCGCGC
oligoF75,ATGCCCGACGGCGAGGATCTCGTCGTGACCCATGGCGATGCCTGCTTGCC
oligoF76,GAATATCATGGTGGAAAATGGCCGCTTTTCTGGATTCATCGACTGTGGCC
oligoF77,GGCTGGGTGTGGCGGACCGCTATCAGGACATAGCGTTGGCTACCCGTGAT
oligoF78,ATTGCTGAAGAGCTTGGCGGCGAATGGGCTGACCGCTTCCTCGTGCTTTA
oligoF79,CGGTATCGCCGCTCCCGATTCGCAGCGCATCGCCTTCTATCGCCTTCTTG
oligoF80,ACGAGTTCTTCTGAGCGGGACTCTGGGGTTCGAAATGACCGACCAAGCGA
oligoF81,CGCCCAACCTGCCATCACGAGATTTCGATTCCACCGCCGCCTTCTATGAA
oligoF82,AGGTTGGGCTTCGGAATCGTTTTCCGGGACGCCGGCTGGATGATCCTCCA
oligoF83,GCGCGGGGATCTCATGCTGGAGTTCTTCGCCCACCCCGGGCATGACCAAA
oligoF84,ATCCCTTAACGTGAGTTTTCGTTCCACTGAGCGTCAGACCCCGTAGAAAA
oligoF85,GATCAAAGGATCTTCTTGAGATCCTTTTTTTCTGCGCGTAATCTGCTGCT
oligoF86,TGCAAACAAAAAAACCACCGCTACCAGCGGTGGTTTGTTTGCCGGATCAA
oligoF87,GAGCTACCAACTCTTTTTCCGAAGGTAACTGGCTTCAGCAGAGCGCAGAT
oligoF88,ACCAAATACTGTCCTTCTAGTGTAGCCGTAGTTAGGCCACCACTTCAAGA
oligoF89,ACTCTGTAGCACCGCCTACATACCTCGCTCTGCTAATCCTGTTACCAGTG
oligoF90,GCTGCTGCCAGTGGCGATAAGTCGTGTCTTACCGGGTTGGACTCAAGACG
oligoF91,ATAGTTACCGGATAAGGCGCAGCGGTCGGGCTGAACGGGGGGTTCGTGCA
oligoF92,CACAGCCCAGCTTGGAGCGAACGACCTACACCGAACTGAGATACCTACAG
oligoF93,CGTGAGCTATGAGAAAGCGCCACGCTTCCCGAAGGGAGAAAGGCGGACAG
oligoF94,GTATCCGGTAAGCGGCAGGGTCGGAACAGGAGAGCGCACGAGGGAGCTTC

FIG. 5C oligoF96,TGACTTGAGCGTCGATTTTTGTGATGCTCGTCAGGGGGGCGGAGCCTATG
oligoR01,CATCACAAAAATCGACGCTCAAGTCAGAGGTGGCGAAACCCGACAGGACT
oligoR02,ATAAAGATACCAGGCGTTTCCCCCTGGAAGCTCCCTCGTGCGCTCTCCTG
oligoR03,TTCCGACCCTGCCGCTTACCGGATACCTGTCCGCCTTTCTCCCTTCGGGA
oligoR04,AGCGTGGCGCTTTCTCATAGCTCACGCTGTAGGTATCTCAGTTCGGTGTA
oligoR05,GGTCGTTCGCTCCAAGCTGGGCTGTGTGCACGAACCCCCCGTTCAGCCCG
oligoR06,ACCGCTGCGCCTTATCCGGTAACTATCGTCTTGAGTCCAACCCGGTAAGA
oligoR07,CACGACTTATCGCCACTGGCAGCAGCCACTGGTAACAGGATTAGCAGAGC
oligoR08,GAGGTATGTAGGCGGTGCTACAGAGTTCTTGAAGTGGTGGCCTAACTACG
oligoR09,GCTACACTAGAAGGACAGTATTTGGTATCTGCGCTCTGCTGAAGCCAGTT
oligoR10,ACCTTCGGAAAAAGAGTTGGTAGCTCTTGATCCGGCAAACAAACCACCGC
oligoR11,TGGTAGCGGTGGTTTTTTTGTTTGCAAGCAGCAGATTACGCGCAGAAAAA
oligoR12,AAGGATCTCAAGAAGATCCTTTGATCTTTTCTACGGGGTCTGACGCTCAG
oligoR13,TGGAACGAAAACTCACGTTAAGGGATTTTGGTCATGCCCGGGGTGGGCGA
oligoR14,AGAACTCCAGCATGAGATCCCCGCGCTGGAGGATCATCCAGCCGGCGTCC
oligoR15,CGGAAAACGATTCCGAAGCCCAACCTTTCATAGAAGGCGGCGGTGGAATC
oligoR16,GAAATCTCGTGATGGCAGGTTGGGCGTCGCTTGGTCGGTCATTTCGAACC
oligoR17,CCAGAGTCCCGCTCAGAAGAACTCGTCAAGAAGGCGATAGAAGGCGATGC
oligoR18,GCTGCGAATCGGGAGCGGCGATACCGTAAAGCACGAGGAAGCGGTCAGCC
oligoR19,CATTCGCCGCCAAGCTCTTCAGCAATATCACGGGTAGCCAACGCTATGTC
oligoR20,CTGATAGCGGTCCGCCACACCCAGCCGGCCACAGTCGATGAATCCAGAAA
oligoR21,AGCGGCCATTTTCCACCATGATATTCGGCAAGCAGGCATCGCCATGGGTC
oligoR22,ACGACGAGATCCTCGCCGTCGGGCATGCGCGCCTTGAGCCTGGCGAACAG
oligoR23,TTCGGCTGGCGCGAGCCCCTGATGCTCTTCGTCCAGATCATCCTGATCGA
oligoR24,CAAGACCGGCTTCCATCCGAGTACGTGCTCGCTCGATGCGATGTTTCGCT
oligoR25,TGGTGGTCGAATGGGCAGGTAGCCGGATCAAGCGTATGCAGCCGCCGCAT
oligoR26,TGCATCAGCCATGATGGATACTTTCTCGGCAGGAGCAAGGTGAGATGACA
oligoR27,GGAGATCCTGCCCCGGCACTTCGCCCAATAGCAGCCAGTCCCTTCCCGCT
oligoR28,TCAGTGACAACGTCGAGCACAGCTGCGCAAGGAACGCCCGTCGTGGCCAG
oligoR29,CCACGATAGCCGCGCTGCCTCGTCCTGCAGTTCATTCAGGGCACCGGACA
oligoR30,GGTCGGTCTTGACAAAAAGAACCGGGCGCCCCTGCGCTGACAGCCGGAAC
oligoR31,ACGGCGGCATCAGAGCAGCCGATTGTCTGTTGTGCCCAGTCATAGCCGAA

FIG. 5D oligoR33, CAATCATGCGAAACGATCCTCATCCTGTCTCTTGATCAGATCTTGATCCC
oligoR34, CTGCGCCATCAGATCCTTGGCGGCAAGAAAGCCATCCAGTTTACTTTGCA
oligoR35, GGGCTTCCCAACCTTACCAGAGGGCGCCCCAGCTGGCAATTCCGGTTCGC
oligoR36, TTGCTGTCCATAAAACCGCCCAGTCTAGCTATCGCCATGTAAGCCCACTG
oligoR37, CAAGCTACCTGCTTTCTCTTTGCGCTTGCGTTTTCCCTTGTCCAGATAGC
oligoR38, CCAGTAGCTGACATTCATCCGGGGTCAGCACCGTTTCTGCGGACTGGCTT
pligoR39, TCTACGTGTTCCGCTTCCTTTAGCAGCCCTTGCGCCCTGAGTGCTTGCGG
oligoR40, CAGCGTGAAGCTTTTTAGAAAAATAAACAAATAGGGGTTCCGCGCACATT
oligoR41, TCCCCGAAAAGTGCCACCTGACGTCTAAGAAACCATTATTATCATGACAT
oligoR42, TAACCTATAAAAATAGGCGTATCACGAGGCCCTTTCGTCTCGCGCGTTTC
oligoR43, GGTGATGACGGTGAAAACCTCTGACACATGCAGCTCCCGGAGACGGTCAC
oligoR44, AGCTTGTCTGTAAGCGGATGCCGGGAGCAGACAAGCCCGTCAGGGCGCGT
oligoR45, CAGCGGGTGTTGGCGGGTGTCGGGGCTGGCTTAACTATGCGGCATCAGAG
oligoR46, CAGATTGTACTGAGAGTGCACCATATGCGGTGTGAAATACCGCACAGATG
oligoR47, CGTAAGGAGAAAATACCGCATCAGGCGCCATTCGCCATTCAGGCTGCGCA
oligoR48, ACTGTTGGGAAGGGCGATCGGTGCGGGCCTCTTCGCTATTACGCCAGCTG
oligoR49, GCGAAAGGGGGATGTGCTGCAAGGCGATTAAGTTGGGTAACGCCAGGGTT
oligoR50, TTCCCAGTCACGACGTTGTAAAACGACGGCCAGTGAATTCTCATCTTATT
oligoR51, AATCAGATAAAATATTTCTAGAGGATCCCCAAAAAGGCAATCTAATATAG
oligoR52, AAATTGCCTTTAATTTTATTATGGTAAATTCATTTCGATTTTTTGGTTCA
oligoR53, ACATATCAATAATATCTTTTACATCTTTAATATCGGACATTGATTCAAAG
oligoR54, GATAATAAAATATTTTTAGACCCTGTTTTTTCCACTGCTAATTTTGTCGA
oligoR55, TTCATAATAGTCATCATGAGACCCAACTGCATTCTCTTCAATAATGCAGT
oligoR56, TAATTTTTTTCATCTCTGTCCATTTGAGGGTAAGTTTCAGTGATATAGTCT
oligoR57, TTTAAGTATTCTCTCACTTCTTCTTGAGCCGTACTTCTATCAGCATTTAA
oligoR58, GTTCGCAATTACAGTTAATTGATGATCAACATCCGAAATATCAATACCAT
oligoR59, ATTGTTGTGCTGTTTATTATATAGAATTGCATAGCGTTCTTTGGTTTCT
oligoR60, AAATTATCCTCCCACTTAAATGTTAAAGGCAGTGCCTTTTTCGCTGCCCA
oligoR61, CATGACGACTTCTTTTGATGTAGCGGATACATATTGCTTAGGTCCATTCT
oligoR62, CACTGTAACAGTGTGGATTAATTGAAACCTTTGGAAAATCATAAAAGTCG
oligoR63, TTTTGGGGATGACAATAACCTGTAGTTAATGCGTCATTAATTATTTCATA
oligoR64, GCATGCTTCAAATTGTTGTTGCCTTGATGAGATATGACGTCTAAAAAATT

FIG. 5E oligoR66, TCTGACATTTGATCTAATAAACTGGCTTCTTCTGCTACACGTACAGGGTG
oligoR67, ATGGGTGGTAATTACTTGATTTAATGAACCAATATGTAATTTATTTGTTA
oligoR68, ACCCTAATAAAAAACCAGCTGCGGTAATAGGTGCTCCAACAATACCATTT
oligoR69, TTTGAAAAGTGATGTTCATTAACAAAGGCAGTATTAAAATGATATTTAGT
oligoR70, TGAATCAATTAACGTGACAGTCTTTACCATATTATCCAACGTTTCTTCAG
oligoR71, ATGTTATTCCATCTTTCTGAAAGTTTAGAAAAAATAATCCAAATTTCATA
oligoR72, ACTTGTTCCTTATTATCTCTAGTATCAAATAAGTAATTTATTTAGGTTCT
oligoR73, TTTAAGAAAGGAGCGACTTGTGTCATAAAGCGTCGCATGGAAGCAATTAT
oligoR74, TTCATCTTCAGTTCCATTAGCTTCAAATCCGCATGTAATGTTTGTAATAC
oligoR75, CCGTTGCATCAATATCACGTTGAATGATTTCAATACACTGCTCAGGAGTG
oligoR76, CCTACAGGGTTAATACCATTGCTATAATCAACACGTCGATTGGTGTTTGT
oligoR77, ATGTCCTTGTAAAACAAAATCACGCCATTGACCTTTATGATAATCATAAC
oligoR78, CACGAGTTTGATTGCTATCATTAAAGATATTGGTCGCATTTACATATGAG
oligoR79, TCATACCAATTTTTCAGAAACTCCCGACAAACATCTTGCGCCTTTTGTGC
oligoR80, ATCATCATCAACAGAACAAATATAAGTCATACAATGATCTATTTTAGATA
oligoR81, TATCATGACCATATTCTGTCGCAATTTCATTATAGAGTTCCATCTGTGCT
oligoR82, TTTTTTTCATTAGTACCAATAATCCAACTAAGAACCATTGGTAGCCCTTG
oligoR83, TATTGCTAGCCATTCTGTCGTACTTGCGGACTCAGCAGTCATACAGGTTG
oligoR84, GTACATTTTTTGAGTACACTTTGGGATATACATCAACCTTAGGAAATTGA
oligoR85, ATGTAATCACTATCAGAGCTAATGGTTCCTGTCTGTAAGCTTTCCATTAT
oligoR86, CATCTGGTAGAAATTTTGAGTAATTGCTCGAGACTCTTCCATATCAACAC
oligoR87, CAAATACTCGAAAATCTTTATGGTATAGCCCTCGAACGGTTCCAAAATTA
oligoR88, AAACGACCTTTCGACATTTGATCTAATAATAAAACGTCTTCTAACTGTCG
oligoR89, AACTGGGTGTGCTGTCGGAATAACAACCCCCATAGTGCCAACATTTAATG
oligoR90, TTTTAGTTCTTCCTAACAGGTTAGCCGCAGCAACAAATAAATTTCCCGTA
oligoR91, AGACCAAACTCTGTAAAATGATGTTCTAAGGTCCAATATGTATCAAACCC
oligoR92, TACTCTTCTGAGGCGATACCAAGCCGAACAAAGCGATCCATTACTTAGCT
oligoR93, TATGAGTTTCACCTGGTGGTTGATACGAAAAACAAATATTTCCAAACTTC
oligoR94, ATACTCTATTCCTTTTTGGTGATTCTGTTTATTTAAGCCAATTCTAATAA
oligoR95, TTCATTTTCAATTTCATTTTTTAATCTACGCTCCTTAACAGTAATACTTG
oligoR96, TAACGTCCTCAAATCGAGGTAAGCTTCATAGGCTCCGCCCCCCTGACGAG

FIG. 5F

Instruction set for 192 oligos (96 pairs).

1.   -F A1 --> -C A1
   -F A2 --> -C A2
   -F A3 --> -C A3
   -F A4 --> -C A4
   repeat with all wells to H12
   -R A1 --> -C A1
   -R A2 --> -C A2
   -R A3 --> -C A3
   -R A4 --> -C A4
   repeat with all wells to H12

All remaining operations on -C plate

2.   A1   --> A2
   A3   --> A4
   A5   --> A6
   A7   --> A8
   A9   --> A10
   A11 --> A12
   repeat with each letter 3.   A2   --> A4
   A6   --> A8
   A10 --> A12
   repeat with each letter

```
program Syn_Gene_Formatter (input, output f, g, h);

{Synthetic Gene Formatting Program}
{This is a draft experimental program designed to break
down a designer gene or genome}{into oligonucleotides for
synthesis.  The program is for complete synthetic
designer gene}{construction.  The program is based upon
an original program for formatting DNA sequences}{written
in 1988 by G. Evans for DNA analysis and formatting}
{This program is copyright (c) 1997 Glen A. Evans.  All
rights reserved} const
  maxlength = 5000; {maximum length of sequence}
  searchlength = 10; {maximum length of search string} var
  f: text; {inputfile of sequence}
  g: text; {output file of sequence}
  h: text; {output file of sequence}

{arrays for sequence formatting} dna: array[1..maxlength] of char;
  rdna: array[1..maxlength] of char;
  oligo: array[1..100] of char;

i, k, seqlength: integer;
  nucin: char;
  oligolength, offset: integer;

infile, outfile: string
```

FIG. 7A

```
procedure initialize;
{This procedure initializes the program and opens the
input file} var
  s: string begin
  repeat
   write('>')
   readin(s);
  until length(s) = 0;
  writein('Welcome to Syn_Gene_Formatter Version 1.0 -
copyright (c) Glen A. Evans 1997');
  write('Enter the input file name: ');
  readin(infile);
  write('Enter the outputfile name: ');
  readin(outfile);
  write('Enter the length of oligos you wish to use:
');
  readin(oligolength);
  write('Enter the reverse oligo offset value: ');
  readin(offset);
  writein('Thank you. ');
  write('The program will now format the sequence into
oligoncleotide fragments of length ');
  write(oligolength);
  writein;
  writein;

end; {initialize} procedure readinseq;
  var
 j: integer;
  nuc: char;
```

FIG. 7B

```
begin
  writeln('reading input file');
  seqlength:=1;
  while not eof(f) do
   begin
    read(f, nuc);
    if nuc <> ' 'then
     begin
      if nuc = 'G' then
        dna[seqlength] := nuc;
      if nuc = 'A' then
        dna[seqlength] := nuc;
      if nuc = 'T' then
        dna[seqlength] := nuc;
      if nuc = 'C' then
        dna[seqlength] := nuc;
      if nuc = 'X' then
        dna[seqlength] := nuc;
      if nuc = 'N' then
        dna[seqlength] := nuc;
      seqlength : = seqlength + 1;
     end;
   end;

seqlength := seqlength - 1;

end; {readinseq} procedure readinfile;

begin
reset(f, infile);
readinseq;
close(f);
```

FIG. 7C

```
end; {readinfile} procedure writeforseq;

var i, h, b, on: integer;

begin
  write ('fragmenting sequence into forward oligos');
  b:= 1;
  on:= 1;
  rewrite(g, outfile);
  writein(g, infile);

while b < seqlength + 1 do
  begin
    write('.');
    write(g, 'Foligo No.', on, '.      ');
    begin
      for h:= 1 to oligolength do
        begin
          write(g, dna[b]]);
          b:= b + 1;
        end;
      on:= on + 1;
      writein(g);
    end;
  end;
writeln;

end;    {writeforseq}
```

FIG. 7D

```
procedure reverseseq;

{This procedure generates the reverse complement of the
sequence} var i, h, b, a, on: integer;

begin write('generating the reverse complement');
b := seqlength;
for a := 1 to seqlength do
  begin
    if dna[b] = 'G' then
      rdna[a] := 'C';
    if dna[b] = 'A' then
      rdna[a] := 'T';
    if dna[b] = 'T' then
      rdna[a] := 'A';
    if dna[b] = 'C' then
      rdna[a] := 'G';
    b := b - 1;
    write('.');
  end;
writeln;

end;   {reverseseq} procedure writerevseq;
```

FIG. 7E

{This procedure fragments the reverse complement sequence starting at the offset value} var i, h, b, on: integer;

begin
    write ('fragmenting sequence into reverse oligos');

on := 1;
b := offset;

while b < seqlength do begin
    writeln(g);
    write(g, 'Roligo No.', on, '.   ');
    begin
     for h := 1 to oligolength do
     begin
      write(g, rdna[b]);
      b := b + 1;
     end;
     on := on + 1;
     write('.');
    end;
end;
   end; {writerevseq} procedure finaloligo;

var
     b, a: integer;

FIG. 7F

```
begin
  writein;
  writein('generating the last portion of the final
oligo...');
    for a := 1 to offset do
      begin
        write(g, rdna[a])

end;
    writein(g);
    close(g);

end; {finaloligo} begin {main} initialize;
  readinfile;
  writeforseq;
  reverseseq;
  writerevseq;
  finaloligo;
  writein('processing completed');
  writein('Have a nice day . ');

end. {main}
```

FIG. 7G

SEQUENCE LISTING

```
<160> NUMBER OF SEQ ID NOS: 193

<210> SEQ ID NO 1
<211> LENGTH: 4800
<212> TYPE: DNA
<213> ORGANISM: Artificial Sequence
<220> FEATURE:
<223> OTHER INFORMATION: Synthetic plasmid

<400> SEQUENCE: 1
aagcttacct cgatttgagg acgttacaag tattactgtt aaggagcgta gattaaaaaa      60
tgaaattgaa aatgaattat tagaattggc ttaaataaac agaatcacca aaaaggaata     120
gagtatgaag tttggaaata tttgtttttc gtatcaacca ccaggtgaaa ctcataagct     180
aagtaatgga tcgctttgtt cggcttggta tcgcctcaga agagtagggt ttgatacata     240
ttggacctta gaacatcatt ttacagagtt tggtcttacg ggaaatttat ttgttgctgc     300
ggctaacctg ttaggaagaa ctaaaacatt aaatgttggc actatggggg ttgttattcc     360
gacagcacac ccagttcgac agttagaaga cgtttttatta ttagatcaaa tgtcgaaagg     420 tcgtttttaat tttggaaccg ttcgagggct ataccataaa gattttcgag tatttggtgt     480
tgatatggaa gagtctcgag caattactca aaatttctac cagatgataa tggaaagctt     540
acagacagga accattagct ctgatagtga ttacattcaa tttcctaagg ttgatgtata     600
tcccaaagtg tactcaaaaa atgtaccaac ctgtatgact gctgagtccg caagtacgac     660
agaatggcta gcaatacaag ggctaccaat ggttcttagt tggattattg gtactaatga     720 aaaaaagca cagatggaac tctataatga aattgcgaca gaatatggtc atgatatatc     780
taaaatagat cattgtatga cttatatttg ttctgttgat gatgatgcac aaaaggcgca     840
agatgtttgt cgggagtttc tgaaaaattg gtatgactca tatgtaaatg cgaccaatat     900
ctttaatgat agcaatcaaa ctcgtggtta tgattatcat aaaggtcaat ggcgtgattt     960
tgttttacaa ggacatacaa acaccaatcg acgtgttgat tatagcaatg gtattaaccc    1020
tgtaggcact cctgagcagt gtattgaaat cattcaacgt gatattgatg caacgggtat    1080
tacaaacatt acatgcggat ttgaagctaa tggaactgaa gatgaaataa ttgcttccat    1140
```

-continued

| | |
|---|---|
| gcgacgcttt atgacacaag tcgctccttt cttaaaagaa cctaaataaa ttacttattt | 1200 |
| gatactagag ataataagga acaagttatg aaatttggat tatttttct aaactttcag | 1260 |
| aaagatggaa taacatctga agaaacgttg gataatatgg taaagactgt cacgttaatt | 1320 |
| gattcaacta aatatcattt taatactgcc tttgttaatg aacatcactt ttcaaaaaat | 1380 |
| ggtattgttg gagcacctat taccgcagct ggttttttat tagggttaac aaataaatta | 1440 |
| catattggtt cattaaatca gtaattacc acccatcacc ctgtacgtgt agcagaagaa | 1500 |
| gccagtttat tagatcaaat gtcagaggga cgcttcattc ttggttttag tgactgcgaa | 1560 |
| agtgatttcg aaatggaatt ttttagacgt catatctcat caaggcaaca acaatttgaa | 1620 |
| gcatgctatg aaataattaa tgacgcatta actacaggtt attgtcatcc ccaaaacgac | 1680 |
| ttttatgatt ttccaaaggt ttcaattaat ccacactgtt acagtgagaa tggacctaag | 1740 |
| caatatgtat ccgctacatc aaaagaagtc gtcatgtggg cagcgaaaaa ggcactgcct | 1800 |
| ttaacattta agtgggagga taatttagaa accaaagaac gctatgcaat tctatataat | 1860 |
| aaaacagcac aacaatatgg tattgatatt tcggatgttg atcatcaatt aactgtaatt | 1920 |
| gcgaacttaa atgctgatag aagtacggct caagaagaag tgagagaata cttaaaagac | 1980 |
| tatatcactg aaacttaccc tcaaatggac agagatgaaa aaattaactg cattattgaa | 2040 |
| gagaatgcag ttgggtctca tgatgactat tatgaatcga caaaattagc agtggaaaaa | 2100 |
| acagggtcta aaaatatttt attatccttt gaatcaatgt ccgatattaa agatgtaaaa | 2160 |
| gatattattg atatgttgaa ccaaaaaatc gaaatgaatt taccataata aaattaaagg | 2220 |
| caatttctat attagattgc cttttgggg atcctctaga aatatttat ctgattaata | 2280 |
| agatgagaat tcactggccg tcgttttaca acgtcgtgac tgggaaaacc ctggcgttac | 2340 |
| ccaacttaat cgccttgcag cacatccccc tttcgccagc tggcgtaata gcgaagaggc | 2400 |
| ccgcaccgat cgcccttccc aacagttgcg cagcctgaat ggcgaatggc gcctgatgcg | 2460 |
| gtattttctc cttacgcatc tgtgcggtat ttcacaccgc atatggtgca ctctcagtac | 2520 |
| aatctgctct gatgccgcat agttaagcca gccccgacac ccgccaacac ccgctgacgc | 2580 |
| gccctgacgg gcttgtctgc tcccggcatc cgcttacaga caagctgtga ccgtctccgg | 2640 |
| gagctgcatg tgtcagaggt tttcaccgtc atcaccgaaa cgcgcgagac gaaagggcct | 2700 |
| cgtgatacgc ctatttttat aggttaatgt catgataata atggtttctt agacgtcagg | 2760 |
| tggcactttt cggggaaatg tgcgcggaac ccctatttgt ttatttttct aaaaagcttc | 2820 |
| acgctgccgc aagcactcag ggcgcaaggg ctgctaaagg aagcggaaca cgtagaaagc | 2880 |
| cagtccgcag aaacggtgct gaccccggat gaatgtcagc tactgggcta tctggacaag | 2940 |
| ggaaaacgca agcgcaaaga gaaagcaggt agcttgcagt gggcttacat ggcgatagct | 3000 |
| agactgggcg gttttatgga cagcaagcga accggaattg ccagctgggg cgccctctgg | 3060 |
| taaggttggg aagccctgca agtaaactg gatggctttc ttgccgccaa ggatctgatg | 3120 |
| gcgcagggga tcaagatctg atcaagagac aggatgagga tcgtttcgca tgattgaaca | 3180 |
| agatggattg cacgcaggtt ctccggccgc ttgggtggag aggctattcg gctatgactg | 3240 |
| ggcacaacag acaatcggct gctctgatgc cgccgtgttc cggctgtcag cgcaggggcg | 3300 |
| cccggttctt tttgtcaaga ccgacctgtc cggtgccctg aatgaactgc aggacgaggc | 3360 |
| agcgcggcta tcgtggctgg ccacgacggg cgttccttgc gcagctgtgc tcgacgttgt | 3420 |
| cactgaagcg ggaagggact ggctgctatt gggcgaagtg ccggggcagg atctcctgtc | 3480 |
| atctcacctt gctcctgccg agaaagtatc catcatggct gatgcaatgc ggcggctgca | 3540 |

```
tacgcttgat ccggctacct gcccattcga ccaccaagcg aaacatcgca tcgagcgagc    3600
acgtactcgg atggaagccg tcttgtcga tcaggatgat ctggacgaag agcatcaggg    3660
gctcgcgcca gccgaactgt tcgccaggct caaggcgcgc atgcccgacg gcgaggatct    3720
cgtcgtgacc catggcgatg cctgcttgcc gaatatcatg gtggaaaatg ccgcttttc    3780 tggattcatc gactgtggcc ggctgggtgt ggcggaccgc tatcaggaca tagcgttggc    3840
tacccgtgat attgctgaag agcttggcgg cgaatgggct gaccgcttcc tcgtgcttta    3900
cggtatcgcc gctcccgatt cgcagcgcat cgccttctat cgccttcttg acgagttctt    3960
ctgagcggga ctctggggtt cgaaatgacc gaccaagcga cgcccaacct gccatcacga    4020
gatttcgatt ccaccgccgc cttctatgaa aggttgggct tcggaatcgt tttccgggac    4080
gccggctgga tgatcctcca gcgcggggat ctcatgctgg agttcttcgc ccaccccggg    4140
catgaccaaa atcccttaac gtgagttttc gttccactga gcgtcagacc ccgtagaaaa    4200
gatcaaagga tcttcttgag atcctttttt tctgcgcgta atctgctgct tgcaaacaaa    4260
aaaaccaccg ctaccagcgg tggtttgttt gccggatcaa gagctaccaa ctctttttcc    4320
gaaggtaact ggcttcagca gagcgcagat accaaatact gtccttctag tgtagccgta    4380
gttaggccac cacttcaaga actctgtagc accgcctaca tacctcgctc tgctaatcct    4440
gttaccagtg gctgctgcca gtggcgataa gtcgtgtctt accgggttgg actcaagacg    4500
atagttaccg gataaggcgc agcggtcggg ctgaacgggg ggttcgtgca cacagcccag    4560
cttggagcga acgacctaca ccgaactgag atacctacag cgtgagctat gagaaagcgc    4620
cacgcttccc gaagggagaa aggcggacag gtatccggta agcggcaggg tcggaacagg    4680
agagcgcacg agggagcttc cagggggaaa cgcctggtat ctttatagtc ctgtcgggtt    4740
tcgccacctc tgacttgagc gtcgattttt gtgatgctcg tcagggggc ggagcctatg    4800

<210> SEQ ID NO 2
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 2
aagcttacct cgatttgagg acgttacaag tattactgtt aaggagcgta                50

<210> SEQ ID NO 3
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 3
gattaaaaaa tgaaattgaa aatgaattat tagaattggc ttaaataaac                50

<210> SEQ ID NO 4
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 4
agaatcacca aaaaggaata gagtatgaag tttggaaata tttgttttc                 50
```

```
<210> SEQ ID NO 5
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 5
gtatcaacca ccaggtgaaa ctcataagct aagtaatgga tcgctttgtt            50

<210> SEQ ID NO 6
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 6
cggcttggta tcgcctcaga agagtagggt ttgatacata ttggaccttga           50

<210> SEQ ID NO 7
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 7
gaacatcatt ttacagagtt tggtcttacg ggaaatttat tgttgctgc             50

<210> SEQ ID NO 8
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 8
ggctaacctg ttaggaagaa ctaaaacatt aaatgttggc actatggggg            50

<210> SEQ ID NO 9
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 9
ttgttattcc gacagcacac ccagttcgac agttagaaga cgttttatta            50

<210> SEQ ID NO 10
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 10
ttagatcaaa tgtcgaaagg tcgttttaat tttggaaccg ttcgagggct            50

<210> SEQ ID NO 11
<211> LENGTH: 50
<212> TYPE: DNA
<213> ORGANISM: Artificial Sequence
<220> FEATURE:
<223> OTHER INFORMATION: Synthetic Oligonucleotide
```

```
<400> SEQUENCE: 11
ataccataaa gattttcgag tatttggtgt tgatatggaa gagtctcgag            50

<210> SEQ ID NO 12
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 12
caattactca aaatttctac cagatgataa tggaaagctt acagacagga            50

<210> SEQ ID NO 13
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 13
accattagct ctgatagtga ttacattcaa tttcctaagg ttgatgtata            50

<210> SEQ ID NO 14
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 14
tcccaaagtg tactcaaaaa atgtaccaac ctgtatgact gctgagtccg            50

<210> SEQ ID NO 15
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 15
caagtacgac agaatggcta gcaatacaag ggctaccaat ggttcttagt            50

<210> SEQ ID NO 16
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 16
tggattattg gtactaatga aaaaaaagca cagatggaac tctataatga            50

<210> SEQ ID NO 17
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 17
aattgcgaca gaatatggtc atgatatatc taaaatagat cattgtatga            50

<210> SEQ ID NO 18
<211> LENGTH: 50
```

<212> TYPE: DNA
<213> ORGANISM: Artificial Sequence
<220> FEATURE:
<223> OTHER INFORMATION: Synthetic Oligonucleotide

<400> SEQUENCE: 18
cttatatttg ttctgttgat gatgatgcac aaaaggcgca agatgtttgt          50

<210> SEQ ID NO 19
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 19
cgggagtttc tgaaaaattg gtatgactca tatgtaaatg cgaccaatat          50

<210> SEQ ID NO 20
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 20
ctttaatgat agcaatcaaa ctcgtggtta tgattatcat aaaggtcaat          50

<210> SEQ ID NO 21
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 21
ggcgtgattt tgttttacaa ggacatacaa acaccaatcg acgtgttgat          50

<210> SEQ ID NO 22
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 22
tatagcaatg gtattaaccc tgtaggcact cctgagcagt gtattgaaat          50

<210> SEQ ID NO 23
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 23
cattcaacgt gatattgatg caacgggtat tacaaacatt acatgcggat          50

<210> SEQ ID NO 24
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 24
ttgaagctaa tggaactgaa gatgaaataa ttgcttccat gcgacgcttt            50

<210> SEQ ID NO 25
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 25
atgacacaag tcgctccttt cttaaaagaa cctaaataaa ttacttattt            50

<210> SEQ ID NO 26
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 26
gatactagag ataataagga acaagttatg aaatttggat tatttttcct            50

<210> SEQ ID NO 27
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 27
aaactttcag aaagatggaa taacatctga agaaacgttg gataatatgg            50

<210> SEQ ID NO 28
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 28
taaagactgt cacgttaatt gattcaacta aatatcattt taatactgcc            50

<210> SEQ ID NO 29
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 29
tttgttaatg aacatcactt ttcaaaaaat ggtattgttg gagcacctat            50

<210> SEQ ID NO 30
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 30
taccgcagct ggttttttat tagggttaac aaataaatta catattggtt            50

<210> SEQ ID NO 31
<211> LENGTH: 50

<212> TYPE: DNA
<213> ORGANISM: Artificial Sequence
<220> FEATURE:
<223> OTHER INFORMATION: Synthetic Oligonucleotide

<400> SEQUENCE: 31
cattaaatca agtaattacc acccatcacc ctgtacgtgt agcagaagaa          50

<210> SEQ ID NO 32
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 32
gccagtttat tagatcaaat gtcagaggga cgcttcattc ttggttttag          50

<210> SEQ ID NO 33
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 33
tgactgcgaa agtgatttcg aaatggaatt ttttagacgt catatctcat          50

<210> SEQ ID NO 34
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 34
caaggcaaca acaatttgaa gcatgctatg aaataattaa tgacgcatta          50

<210> SEQ ID NO 35
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 35
actacaggtt attgtcatcc ccaaaacgac ttttatgatt ttccaaaggt          50

<210> SEQ ID NO 36
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 36
ttcaattaat ccacactgtt acagtgagaa tggacctaag caatatgtat          50

<210> SEQ ID NO 37
<211> LENGTH: 50
<212> TYPE: DNA
<213> ORGANISM: Artificial Sequence
<220> FEATURE:
<223> OTHER INFORMATION: Synthetic Oligonucleotide

```
<400> SEQUENCE: 37
ccgctacatc aaaagaagtc gtcatgtggg cagcgaaaaa ggcactgcct         50

<210> SEQ ID NO 38
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 38
ttaacattta agtgggagga taatttagaa accaaagaac gctatgcaat         50

<210> SEQ ID NO 39
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 39
tctatataat aaaacagcac aacaatatgg tattgatatt tcggatgttg         50

<210> SEQ ID NO 40
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 40
atcatcaatt aactgtaatt gcgaacttaa atgctgatag aagtacggct         50

<210> SEQ ID NO 41
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 41
caagaagaag tgagagaata cttaaaagac tatatcactg aaacttaccc         50

<210> SEQ ID NO 42
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 42
tcaaatggac agagatgaaa aaattaactg cattattgaa gagaatgcag         50

<210> SEQ ID NO 43
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 43
ttgggtctca tgatgactat tatgaatcga caaaattagc agtggaaaaa         50

<210> SEQ ID NO 44
<211> LENGTH: 50
```

```
<212> TYPE: DNA
<213> ORGANISM: Artificial Sequence
<220> FEATURE:
<223> OTHER INFORMATION: Synthetic Oligonucleotide

<400> SEQUENCE: 44
acagggtcta aaatatttt attatccttt gaatcaatgt ccgatattaa          50

<210> SEQ ID NO 45
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 45
agatgtaaaa gatattattg atatgttgaa ccaaaaaatc gaaatgaatt          50

<210> SEQ ID NO 46
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 46
taccataata aaattaaagg caatttctat attagattgc ctttttgggg          50

<210> SEQ ID NO 47
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 47
atcctctaga aatattttat ctgattaata agatgagaat tcactggccg          50

<210> SEQ ID NO 48
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 48
tcgttttaca acgtcgtgac tgggaaaacc ctggcgttac ccaacttaat          50

<210> SEQ ID NO 49
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 49
cgccttgcag cacatccccc tttcgccagc tggcgtaata gcgaagaggc          50

<210> SEQ ID NO 50
<211> LENGTH: 50
<212> TYPE: DNA
<213> ORGANISM: Artificial Sequence
<220> FEATURE:
<223> OTHER INFORMATION: Synthetic Oligonucleotide
```

<400> SEQUENCE: 50
ccgcaccgat cgcccttccc aacagttgcg cagcctgaat ggcgaatggc　　　　　　50

<210> SEQ ID NO 51
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 51
gcctgatgcg gtattttctc cttacgcatc tgtgcggtat ttcacaccgc　　　　　　50

<210> SEQ ID NO 52
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 52
atatggtgca ctctcagtac aatctgctct gatgccgcat agttaagcca　　　　　　50

<210> SEQ ID NO 53
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 53
gccccgacac ccgccaacac ccgctgacgc gccctgacgg gcttgtctgc　　　　　　50

<210> SEQ ID NO 54
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 54
tcccggcatc cgcttacaga caagctgtga ccgtctccgg gagctgcatg　　　　　　50

<210> SEQ ID NO 55
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 55
tgtcagaggt tttcaccgtc atcaccgaaa cgcgcgagac gaaagggcct　　　　　　50

<210> SEQ ID NO 56
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 56
cgtgatacgc ctatttttat aggttaatgt catgataata atggtttctt　　　　　　50

<210> SEQ ID NO 57
<211> LENGTH: 50

```
<212> TYPE: DNA
<213> ORGANISM: Artificial Sequence
<220> FEATURE:
<223> OTHER INFORMATION: Synthetic Oligonucleotide

<400> SEQUENCE: 57
agacgtcagg tggcactttt cggggaaatg tgcgcggaac ccctatttgt          50

<210> SEQ ID NO 58
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 58
ttatttttct aaaaagcttc acgctgccgc aagcactcag ggcgcaaggg          50

<210> SEQ ID NO 59
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 59
ctgctaaagg aagcggaaca cgtagaaagc cagtccgcag aaacggtgct          50

<210> SEQ ID NO 60
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 60
gaccccggat gaatgtcagc tactgggcta tctggacaag ggaaaacgca          50

<210> SEQ ID NO 61
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 61
agcgcaaaga gaaagcaggt agcttgcagt gggcttacat ggcgatagct          50

<210> SEQ ID NO 62
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 62
agactgggcg gttttatgga cagcaagcga accggaattg ccagctgggg          50

<210> SEQ ID NO 63
<211> LENGTH: 50
<212> TYPE: DNA
<213> ORGANISM: Artificial Sequence
<220> FEATURE:
<223> OTHER INFORMATION: Synthetic Oligonucleotide
```

<400> SEQUENCE: 63
cgccctctgg taaggttggg aagccctgca agtaaactg gatggctttc        50

<210> SEQ ID NO 64
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 64
ttgccgccaa ggatctgatg gcgcagggga tcaagatctg atcaagagac        50

<210> SEQ ID NO 65
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 65
aggatgagga tcgtttcgca tgattgaaca agatggattg cacgcaggtt        50

<210> SEQ ID NO 66
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 66
ctccggccgc ttgggtggag aggctattcg gctatgactg ggcacaacag        50

<210> SEQ ID NO 67
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 67
acaatcggct gctctgatgc cgccgtgttc cggctgtcag cgcagggcg        50

<210> SEQ ID NO 68
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 68
cccggttctt tttgtcaaga ccgacctgtc cggtgccctg aatgaactgc        50

<210> SEQ ID NO 69
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 69
aggacgaggc agcgcggcta tcgtggctgg ccacgacggg cgttccttgc        50

<210> SEQ ID NO 70
<211> LENGTH: 50

<212> TYPE: DNA
<213> ORGANISM: Artificial Sequence
<220> FEATURE:
<223> OTHER INFORMATION: Synthetic Oligonucleotide

<400> SEQUENCE: 70
gggcgaagtg ccggggcagg atctcctgtc atctcacctt gctcctgccg          50

<210> SEQ ID NO 71
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 71
gggcgaagtg ccggggcagg atctcctgtc atctcacctt gctcctgccg          50

<210> SEQ ID NO 72
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 72
agaaagtatc catcatggct gatgcaatgc ggcggctgca tacgcttgat          50

<210> SEQ ID NO 73
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 73
ccggctacct gcccattcga ccaccaagcg aaacatcgca tcgagcgagc          50

<210> SEQ ID NO 74
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 74
acgtactcgg atggaagccg gtcttgtcga tcaggatgat ctggacgaag          50

<210> SEQ ID NO 75
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 75
agcatcaggg gctcgcgcca gccgaactgt tcgccaggct caaggcgcgc          50

<210> SEQ ID NO 76
<211> LENGTH: 50
<212> TYPE: DNA
<213> ORGANISM: Artificial Sequence
<220> FEATURE:
<223> OTHER INFORMATION: Synthetic Oligonucleotide -continued

```
<400> SEQUENCE: 76
atgcccgacg gcgaggatct cgtcgtgacc catggcgatg cctgcttgcc          50

<210> SEQ ID NO 77
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 77
gaatatcatg gtggaaaatg gccgcttttc tggattcatc gactgtggcc          50

<210> SEQ ID NO 78
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 78
ggctgggtgt ggcggaccgc tatcaggaca tagcgttggc tacccgtgat          50

<210> SEQ ID NO 79
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 79
attgctgaag agcttggcgg cgaatgggct gaccgcttcc tcgtgcttta          50

<210> SEQ ID NO 80
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 80
cggtatcgcc gctcccgatt cgcagcgcat cgccttctat cgccttcttg          50

<210> SEQ ID NO 81
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 81
acgagttctt ctgagcggga ctctggggtt cgaaatgacc gaccaagcga          50

<210> SEQ ID NO 82
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 82
cgcccaacct gccatcacga gatttcgatt ccaccgccgc cttctatgaa          50

<210> SEQ ID NO 83
<211> LENGTH: 50
```

```
<212> TYPE: DNA
<213> ORGANISM: Artificial Sequence
<220> FEATURE:
<223> OTHER INFORMATION: Synthetic Oligonucleotide

<400> SEQUENCE: 83
aggttgggct tcggaatcgt tttccgggac gccggctgga tgatcctcca          50

<210> SEQ ID NO 84
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 84
gcgcggggat ctcatgctgg agttcttcgc ccaccccggg catgaccaaa          50

<210> SEQ ID NO 85
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 85
atcccttaac gtgagttttc gttccactga gcgtcagacc ccgtagaaaa          50

<210> SEQ ID NO 86
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 86
gatcaaagga tcttcttgag atcctttttt tctgcgcgta atctgctgct          50

<210> SEQ ID NO 87
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 87
tgcaaacaaa aaaccaccg ctaccagcgg tggtttgttt gccggatcaa           50

<210> SEQ ID NO 88
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 88
gagctaccaa ctcttttttcc gaaggtaact ggcttcagca gagcgcagat         50

<210> SEQ ID NO 89
<211> LENGTH: 51
<212> TYPE: DNA
<213> ORGANISM: Artificial Sequence
<220> FEATURE:
<223> OTHER INFORMATION: Synthetic Oligonucleotide
```

<400> SEQUENCE: 89
accaaatact gtccttctag tgtagccgta gttaggccac cacttcaatg a        51

<210> SEQ ID NO 90
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 90
actctgtagc accgcctaca tacctcgctc tgctaatcct gttaccagtg          50

<210> SEQ ID NO 91
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 91
gctgctgcca gtggcgataa gtcgtgtctt accgggttgg actcaagacg          50

<210> SEQ ID NO 92
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 92
atagttaccg gataaggcgc agcggtcggg ctgaacgggg ggttcgtgca          50

<210> SEQ ID NO 93
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 93
cacagcccag cttggagcga acgacctaca ccgaactgag atacctacag          50

<210> SEQ ID NO 94
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 94
cgtgagctat gagaaagcgc cacgcttccc gaagggagaa aggcggacag          50

<210> SEQ ID NO 95
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 95
gtatccggta agcggcaggg tcggaacagg agagcgcacg agggagcttc          50

<210> SEQ ID NO 96
<211> LENGTH: 50

```
<212> TYPE: DNA
<213> ORGANISM: Artificial Sequence
<220> FEATURE:
<223> OTHER INFORMATION: Synthetic Oligonucleotide

<400> SEQUENCE: 96 caggggggaaa cgcctggtat ctttatagtc ctgtcgggtt tcgccacctc         50

<210> SEQ ID NO 97
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 97
tgacttgagc gtcgattttt gtgatgctcg tcaggggggc ggagcctatg         50

<210> SEQ ID NO 98
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 98
catcacaaaa atcgacgctc aagtcagagg tggcgaaacc cgacaggact         50

<210> SEQ ID NO 99
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 99
ataaagatac caggcgtttc ccccctggaag ctccctcgtg cgctctcctg        50

<210> SEQ ID NO 100
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 100
ttccgaccct gccgcttacc ggatacctgt ccgcctttct cccttcggga         50

<210> SEQ ID NO 101
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 101
agcgtggcgc tttctcatag ctcacgctgt aggtatctca gttcggtgta         50

<210> SEQ ID NO 102
<211> LENGTH: 50
<212> TYPE: DNA
<213> ORGANISM: Artificial Sequence
<220> FEATURE:
<223> OTHER INFORMATION: Synthetic Oligonucleotide
```

<400> SEQUENCE: 102
ggtcgttcgc tccaagctgg gctgtgtgca cgaaccccc gttcagcccg            50

<210> SEQ ID NO 103
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 103
accgctgcgc cttatccggt aactatcgtc ttgagtccaa cccggtaaga            50

<210> SEQ ID NO 104
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 104
cacgacttat cgccactggc agcagccact ggtaacagga ttagcagagc            50

<210> SEQ ID NO 105
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 105
gaggtatgta ggcggtgcta cagagttctt gaagtggtgg cctaactacg            50

<210> SEQ ID NO 106
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 106
gctacactag aaggacagta tttggtatct gcgctctgct gaagccagtt            50

<210> SEQ ID NO 107
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 107
accttcggaa aaagagttgg tagctcttga tccggcaaac aaaccaccgc            50

<210> SEQ ID NO 108
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 108
tggtagcggt ggtttttttg tttgcaagca gcagattacg cgcagaaaaa            50

<210> SEQ ID NO 109
<211> LENGTH: 50

```
<212> TYPE: DNA
<213> ORGANISM: Artificial Sequence
<220> FEATURE:
<223> OTHER INFORMATION: Synthetic Oligonucleotide

<400> SEQUENCE: 109
aaggatctca agaagatcct ttgatctttt ctacggggtc tgacgctcag         50

<210> SEQ ID NO 110
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 110
tggaacgaaa actcacgtta agggattttg gtcatgcccg gggtgggcga         50

<210> SEQ ID NO 111
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 111
agaactccag catgagatcc ccgcgctgga ggatcatcca gccggcgtcc         50

<210> SEQ ID NO 112
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 112
cggaaaacga ttccgaagcc caacctttca tagaaggcgg cggtggaatc         50

<210> SEQ ID NO 113
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 113
gaaatctcgt gatggcaggt tgggcgtcgc ttggtcggtc atttcgaacc         50

<210> SEQ ID NO 114
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 114
ccagagtccc gctcagaaga actcgtcaag aaggcgatag aaggcgatgc         50

<210> SEQ ID NO 115
<211> LENGTH: 50
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 115
gctgcgaatc gggagcggcg ataccgtaaa gcacgaggaa gcggtcagcc        50

<210> SEQ ID NO 116
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 116
cattcgccgc caagctcttc agcaatatca cgggtagcca acgctatgtc        50

<210> SEQ ID NO 117
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 117
ctgatagcgg tccgccacac ccagccggcc acagtcgatg aatccagaaa        50

<210> SEQ ID NO 118
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 118
agcggccatt ttccaccatg atattcggca agcaggcatc gccatgggtc        50

<210> SEQ ID NO 119
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 119
acgacgagat cctcgccgtc gggcatgcgc gccttgagcc tggcgaacag        50

<210> SEQ ID NO 120
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 120
ttcggctggc gcgagcccct gatgctcttc gtccagatca tcctgatcga        50

<210> SEQ ID NO 121
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 121
caagaccggc ttccatccga gtacgtgctc gctcgatgcg atgtttcgct        50

<210> SEQ ID NO 122
<211> LENGTH: 50
```

```
<212> TYPE: DNA
<213> ORGANISM: Artificial Sequence
<220> FEATURE:
<223> OTHER INFORMATION: Synthetic Oligonucleotide

<400> SEQUENCE: 122
tggtggtcga atgggcaggt agccggatca agcgtatgca gccgccgcat            50

<210> SEQ ID NO 123
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 123
tgcatcagcc atgatggata ctttctcggc aggagcaagg tgagatgaca            50

<210> SEQ ID NO 124
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 124
ggagatcctg ccccggcact tcgcccaata gcagccagtc ccttcccgct            50

<210> SEQ ID NO 125
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 125
tcagtgacaa cgtcgagcac agctgcgcaa ggaacgcccg tcgtggccag            50

<210> SEQ ID NO 126
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 126
ccacgatagc cgcgctgcct cgtcctgcag ttcattcagg gcaccggaca            50

<210> SEQ ID NO 127
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 127
ggtcggtctt gacaaaaaga accgggcgcc cctgcgctga cagccggaac            50

<210> SEQ ID NO 128
<211> LENGTH: 50
<212> TYPE: DNA
<213> ORGANISM: Artificial Sequence
<220> FEATURE:
<223> OTHER INFORMATION: Synthetic Oligonucleotide
```

-continued

<400> SEQUENCE: 128
acggcggcat cagagcagcc gattgtctgt tgtgcccagt catagccgaa          50

<210> SEQ ID NO 129
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 129
tagcctctcc acccaagcgg ccggagaacc tgcgtgcaat ccatcttgtt          50

<210> SEQ ID NO 130
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 130
caatcatgcg aaacgatcct catcctgtct cttgatcaga tcttgatccc          50

<210> SEQ ID NO 131
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 131
ctgcgccatc agatccttgg cggcaagaaa gccatccagt ttactttgca          50

<210> SEQ ID NO 132
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 132
gggcttccca accttaccag agggcgcccc agctggcaat tccggttcgc          50

<210> SEQ ID NO 133
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 133
ttgctgtcca taaaccgcc cagtctagct atcgccatgt aagcccactg           50

<210> SEQ ID NO 134
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 134
caagctacct gctttctctt tgcgcttgcg ttttcccttg tccagatagc          50

<210> SEQ ID NO 135
<211> LENGTH: 50

```
<212> TYPE: DNA
<213> ORGANISM: Artificial Sequence
<220> FEATURE:
<223> OTHER INFORMATION: Synthetic Oligonucleotide

<400> SEQUENCE: 135
ccagtagctg acattcatcc ggggtcagca ccgtttctgc ggactggctt          50

<210> SEQ ID NO 136
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 136
tctacgtgtt ccgcttcctt tagcagccct tgcgccctga gtgcttgcgg          50

<210> SEQ ID NO 137
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 137
cagcgtgaag cttttagaa aaataaacaa atagggttc cgcgcacatt            50

<210> SEQ ID NO 138
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 138
tccccgaaaa gtgccacctg acgtctaaga aaccattatt atcatgacat          50

<210> SEQ ID NO 139
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 139
taacctataa aataggcgt atcacgaggc cctttcgtct cgcgcgtttc           50

<210> SEQ ID NO 140
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 140
ggtgatgacg gtgaaaacct ctgacacatg cagctcccgg agacggtcac          50

<210> SEQ ID NO 141
<211> LENGTH: 50
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 141
agcttgtctg taagcggatg ccgggagcag acaagcccgt cagggcgcgt          50

<210> SEQ ID NO 142
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 142
cagcgggtgt tggcgggtgt cggggctggc ttaactatgc ggcatcagag          50

<210> SEQ ID NO 143
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 143
cagattgtac tgagagtgca ccatatgcgg tgtgaaatac cgcacagatg          50

<210> SEQ ID NO 144
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 144
cgtaaggaga aaataccgca tcaggcgcca ttcgccattc aggctgcgca          50

<210> SEQ ID NO 145
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 145
actgttggga agggcgatcg gtgcgggcct cttcgctatt acgccagctg          50

<210> SEQ ID NO 146
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 146
gcgaaagggg gatgtgctgc aaggcgatta agttgggtaa cgccagggtt          50

<210> SEQ ID NO 147
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 147
ttcccagtca cgacgttgta aaacgacggc cagtgaattc tcatcttatt          50

<210> SEQ ID NO 148
<211> LENGTH: 50
```

```
<212> TYPE: DNA
<213> ORGANISM: Artificial Sequence
<220> FEATURE:
<223> OTHER INFORMATION: Synthetic Oligonucleotide

<400> SEQUENCE: 148
aatcagataa aatatttcta gaggatcccc aaaaaggcaa tctaatatag          50

<210> SEQ ID NO 149
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 149
aaattgcctt taattttatt atggtaaatt catttcgatt ttttggttca          50

<210> SEQ ID NO 150
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 150
acatatcaat aatatctttt acatctttaa tatcggacat tgattcaaag          50

<210> SEQ ID NO 151
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 151
gataataaaa tattttttaga ccctgttttt tccactgcta attttgtcga         50

<210> SEQ ID NO 152
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 152
ttcataatag tcatcatgag acccaactgc attctcttca ataatgcagt          50

<210> SEQ ID NO 153
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 153 taatttttc atctctgtcc atttgagggt aagtttcagt gatatagtct           50

<210> SEQ ID NO 154
<211> LENGTH: 50
<212> TYPE: DNA
<213> ORGANISM: Artificial Sequence
<220> FEATURE:
<223> OTHER INFORMATION: Synthetic Oligonucleotide
```

<400> SEQUENCE: 154
tttaagtatt ctctcacttc ttcttgagcc gtacttctat cagcatttaa        50

<210> SEQ ID NO 155
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 155
gttcgcaatt acagttaatt gatgatcaac atccgaaata tcaataccat        50

<210> SEQ ID NO 156
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 156
attgttgtgc tgttttatta tatagaattg catagcgttc tttggtttct        50

<210> SEQ ID NO 157
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 157
aaattatcct cccacttaaa tgttaaaggc agtgcctttt tcgctgccca        50

<210> SEQ ID NO 158
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 158
catgacgact tcttttgatg tagcggatac atattgctta ggtccattct        50

<210> SEQ ID NO 159
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 159
cactgtaaca gtgtggatta attgaaacct ttggaaaatc ataaaagtcg        50

<210> SEQ ID NO 160
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 160 ttttgggat gacaataacc tgtagttaat gcgtcattaa ttatttcata        50

<210> SEQ ID NO 161
<211> LENGTH: 50
<212> TYPE: DNA

<213> ORGANISM: Artificial Sequence
<220> FEATURE:
<223> OTHER INFORMATION: Synthetic Oligonucleotide

<400> SEQUENCE: 161
gcatgcttca aattgttgtt gccttgatga gatatgacgt ctaaaaaatt                50

<210> SEQ ID NO 162
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 162
ccatttcgaa atcactttcg cagtcactaa aaccaagaat gaagcgtccc                50

<210> SEQ ID NO 163
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 163
tctgacattt gatctaataa actggcttct tctgctacac gtacagggtg                50

<210> SEQ ID NO 164
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 164
atgggtggta attacttgat ttaatgaacc aatatgtaat ttatttgtta                50

<210> SEQ ID NO 165
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 165
accctaataa aaaccagct gcggtaatag gtgctccaac aataccattt                 50

<210> SEQ ID NO 166
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 166
tttgaaaagt gatgttcatt aacaaaggca gtattaaaat gatatttagt                50

<210> SEQ ID NO 167
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 167
tgaatcaatt aacgtgacag tctttaccat attatccaac gtttcttcag                50

<210> SEQ ID NO 168
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 168
atgttattcc atctttctga aagtttagaa aaaataatcc aaatttcata        50

<210> SEQ ID NO 169
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 169
acttgttcct tattatctct agtatcaaat aagtaattta tttaggttct        50

<210> SEQ ID NO 170
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 170
tttaagaaag gagcgacttg tgtcataaag cgtcgcatgg aagcaattat        50

<210> SEQ ID NO 171
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 171
ttcatcttca gttccattag cttcaaatcc gcatgtaatg tttgtaatac        50

<210> SEQ ID NO 172
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 172
ccgttgcatc aatatcacgt tgaatgattt caatacactg ctcaggagtg        50

<210> SEQ ID NO 173
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 173
cctacagggt taataccatt gctataatca acacgtcgat tggtgtttgt        50

<210> SEQ ID NO 174
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 174
atgtccttgt aaaacaaaat cacgccattg acctttatga taatcataac 50

<210> SEQ ID NO 175
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 175
cacgagtttg attgctatca ttaaagatat tggtcgcatt tacatatgag 50

<210> SEQ ID NO 176
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 176
tcataccaat ttttcagaaa ctcccgacaa acatcttgcg ccttttgtgc 50

<210> SEQ ID NO 177
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 177
atcatcatca acagaacaaa tataagtcat acaatgatct attttagata 50

<210> SEQ ID NO 178
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 178
tatcatgacc atattctgtc gcaatttcat tatagagttc catctgtgct 50

<210> SEQ ID NO 179
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 179 ttttttttcat tagtaccaat aatccaacta agaaccattg gtagcccttg 50

<210> SEQ ID NO 180
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 180
tattgctagc cattctgtcg tacttgcgga ctcagcagtc atacaggttg 50

<210> SEQ ID NO 181
<211> LENGTH: 50

```
<212> TYPE: DNA
<213> ORGANISM: Artificial Sequence
<220> FEATURE:
<223> OTHER INFORMATION: Synthetic Oligonucleotide

<400> SEQUENCE: 181
gtacattttt tgagtacact ttgggatata catcaacctt aggaaattga          50

<210> SEQ ID NO 182
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 182
atgtaatcac tatcagagct aatggttcct gtctgtaagc tttccattat          50

<210> SEQ ID NO 183
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 183
catctggtag aaattttgag taattgctcg agactcttcc atatcaacac          50

<210> SEQ ID NO 184
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 184
caaatactcg aaaatcttta tggtatagcc ctcgaacggt tccaaaatta          50

<210> SEQ ID NO 185
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 185
aaacgacctt tcgacatttg atctaataat aaaacgtctt ctaactgtcg          50

<210> SEQ ID NO 186
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 186
aactgggtgt gctgtcggaa taacaacccc catagtgcca acatttaatg          50

<210> SEQ ID NO 187
<211> LENGTH: 50
<212> TYPE: DNA
<213> ORGANISM: Artificial Sequence
<220> FEATURE:
<223> OTHER INFORMATION: Synthetic Oligonucleotide
```

<400> SEQUENCE: 187 tttagttct tcctaacagg ttagccgcag caacaaataa atttcccgta         50

<210> SEQ ID NO 188
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 188
agaccaaact ctgtaaaatg atgttctaag gtccaatatg tatcaaaccc         50

<210> SEQ ID NO 189
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 189
tactcttctg aggcgatacc aagccgaaca aagcgatcca ttacttagct         50

<210> SEQ ID NO 190
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 190
tatgagtttc acctggtggt tgatacgaaa aacaaatatt tccaaacttc         50

<210> SEQ ID NO 191
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 191
atactctatt cctttttggt gattctgttt atttaagcca attctaataa         50

<210> SEQ ID NO 192
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 192
ttcattttca atttcatttt ttaatctacg ctccttaaca gtaatacttg         50

<210> SEQ ID NO 193
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 193
taacgtcctc aaatcgaggt aagcttcata ggctccgccc ccctgacgag         50

METHOD FOR THE COMPLETE CHEMICAL SYNTHESIS AND ASSEMBLY OF GENES AND GENOMES

This application claims the benefit of No. 60/059,017, filed Sep. 16, 1997.

BACKGROUND OF THE INVENTION

1. Field of the Invention

The present invention relates generally to the fields of oligonucleotide synthesis. More particularly, it concerns the assembly of genes and genomes of completely synthetic artificial organisms.

2. Description of Related Art

Present research and commercial applications in molecular biology are based upon recombinant DNA developed in the 1970's. A critical facet of recombinant DNA is molecular cloning in plasmids, covered under seminal patent of Cohen and Boyer (U.S. Pat. No. 4,740,470 "Biologically functional molecular chimeras"). This patent teaches a method for the "cutting and splicing" of DNA molecules based upon restriction endonucleases, the introduction of these "recombinant" molecules into host cells, and their replication in the bacterial hosts. This technique is the basis of all molecular cloning for research and commercial purposes carried out for the past 20 years and the basis of the field of molecular biology and genetics.

Recombinant DNA technology is a powerfull technology, but is limited in utility to modifications of existing DNA sequences which are modified through 1) restriction enzyme cleavage sites, 2) PAC primers for amplification, 3) site-specific mutagenesis, and other techniques. The creation of an entirely new molecule, or the substantial modification of existing molecules, is extremely time consuming, expensive, requires complex and multiple steps, and in some cases is impossible. Recombinant DNA technology does not permit the creation of entirely artificial molecules, genes, genomes or organisms, but only modifications of naturally-occurring organisms.

Current biotechnology for industrial production, for drug design and development, for potential applications of vaccine development and genetic therapy, and for agricultural and environmental use of recombinant DNA, depends on naturally-occurring organisms and DNA molecules. To create or engineer new or novel functions, or to modify organisms for specialized use (such as producing a human hormone), requires substantially complex, time consuming and difficult manipulations of naturally-occurring DNA molecules. In some cases, changes to naturally-occurring DNA are so complex that they are not possible in practice. Thus, there is a need for technology that allows the creation of novel DNA molecules in a single step without requiring the use of any existing recombinant or naturally-occurring DNA.

SUMMARY OF THE INVENTION

The present invention addresses the limitations in present recombinant nucleic acid manipulations by providing a fast, efficient means for generating practically any nucleic acid sequence, including entire genes, chromosomal segments, chromosomes and genomes. Because this approach is based on an completely synthetic approach, there are no limitations, such as the availability of existing nucleic acids, to hinder the construction of even very large segments of nucleic acid.

Thus, in a first embodiment, there is provided a method for the construction of a double-stranded DNA segment comprising the steps of (i) providing two sets of single-stranded oligonucleotides, wherein (a) the first set comprises the entire plus strand of said DNA segment, (b) the second set comprises the entire minus strand of said DNA segment, and (c) each of said first set of oligonucleotides being complementary to two oligonucleotides of said second set of oligonucleotides, (ii) annealing said first and said second set of oligonucleotides, and (iii) treating said annealed oligonucleotides with a ligating enzyme. Optional steps provide for the synthesis of the oligonucleotide sets and the transformation of host cells with the resulting DNA segment.

In particular embodiments, the DNA segment is 100, 200, 300, 40,, 800, 100, 1500, 200, 4000, 8000, 10000, 12000, 18,000, 20000, 40,000, 80,000; 100,000, $10^6$, $10^7$, $10^8$, $10^9$ or more base pairs in length. Indeed, it is contemplated that the methods of the present invention will be able to create entire artificial genomes of lengths comparable to known bacterial, yeast, viral, mammalian, amphibian, reptilian, avian genomes. In more particular embodiments, the DNA segment is a gene encoding a protein of interest. The DNA segment further may include non-coding elements such as origins of replication, telomeres, promoters, enhancers, transcription and translation start and stop signals, introns, exon splice sites, chromatin scaffold components and other regulatory sequences. The DNA segment may comprises multiple genes, chromosomal segments, chromosomes and even entire genomes. The DNA segments may be derived from prokaryotic or eukaryotic sequences including bacterial, yeast, viral, mammalian, amphibian, reptilian, avian, plants, archebacteria and other DNA containing living organisms.

The oligonucleotide sets preferably are comprised oligonucleotides of between about 15 and 100 bases and more preferably are between about 20 and 50 bases. Specific lengths include, but are not limited to 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64.65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100. Depending on the size, the overlap between the oligonucleotides of the two sets may be designed to be between 5 and 75 bases per oligonucleotide pair.

The oligonucleotides preferably are treated with polynucleotide kinase, for example, T4 polynucleotide kinase. The kinasing can be performed prior to mixing of the oligonucleotides set or after, but before annealing. After annealing, the oligonucleotides are treated with an enzyme having a ligating function. For example, a DNA ligase typically will be employed for this function. However, topoisomerase, which does not require 5' phosphorylation, is rapid and operates at room temperature, and may be used instead of ligase.

In a second embodiment, there is provided a method for construction of a double-stranded DNA segment comprising the steps of (i) providing two sets of single-stranded oligonucleotides, wherein (a) the first set comprises the entire plus strand of said DNA segment, (b) the second set comprises the entire minus strand of said DNA segment, and (c) each of said first set of oligonucleotides being complementary to two oligonucleotides of said second set of oligonucleotides, (ii) annealing pairs of complementary oligonucleotides to produce a set of first annealed products, wherein each pair comprises an oligonucleotide from each of said first and said second sets of oligonucleotides, (iii) annealing pairs of first annealed products having complementary sequences to produce a set of second annealed products, (iv) repeating the process until all annealed products have been annealed into a single DNA segment, and (v) treating said annealed products with ligating enzyme.

In a third embodiment, there is provided a method for the construction of a double-stranded DNA segment comprising the steps of (i) providing two sets of single-stranded oligonucleotides, wherein (a) the first set comprises the entire plus strand of sand DNA segment, (b) the second set comprises the entire minus strand of said DNA segment, and (c) each of said first set of oligonucleotides being complementary to two oligonucleotides of said second set of oligonucleotides, (ii) annealing said the 5' terminal oligonucleotide of said first set of oligonucleotide with the 3' terminal oligonucleotide of said second set of oligonucleotides, (iii) annealing the next most 5' terminal oligonucleotide of said first set of oligonucleotides with the product of step (ii), (iv) annealing the next most 3' terminal oligonucleotide of said second set of oligonucleotides with the product of step (iii), (v) repeating the process until all oligonucleotides of said first and said second sets have been annealed, and (vi) treating said annealed oligonucleotides with ligating enzyme. Optional steps provide for the synthesis of the oligonucleotide sets and the transformation of host cells with the resulting DNA segment. In a preferred embodiment, the 5' terminal oligonucleotide of the first set is attached to a support, which process may include the additional step of removing the DNA segment from the support. The support may be any support known in the art, for example, a microtiter plate, a filter, polystyrene beads, polystyrene tray, magnetic beads, agarose and the like.

Annealing conditions may be adjusted based on the particular strategy used for annealing, the size and composition of the oligonucleotides, and the extent of overlap between the oligonucleotides of the first and second sets. For example, where all the oligonucleotides are mixed together prior to annealing, heating the mixture to 80° C., followed by slow annealing for between 1 to 12 h is conducted. Thus, annealing may be conducted for about 2, about 3, about 4, about 5, about 6, about 7, about 8, about 9, or about 10 h. However, in other embodiments, the annealing time may be as long as 24 h.

With the aid of a computer, the inventor is able to direct synthesis of a vector/gene combination using a high throughput oligonucleotide synthesizer as a set of overlapping component oligonucleotides. The oligonucleotides are assembled using a robotic combinatoric assembly strategy and the assembly ligated using DNA ligase or topoisomerase, followed by transformation into a suitable host strain. In a particular embodiment, this invention generates a set of bacterial strains containing a viable expression vector for all genes in a defined region of the genome. In other embodiments, a yeast or baculovirus expression vector system is also contemplated to allow expression of each gene in a chromosomal region in a eukaryotic host. In yet another embodiment, it the present invention allows one of skill in the art to devise a "designer gene" strategy wherein a gene or genomes or virtually any structure may be readily designed, synthesized and expressed. Thus, eventually the technology described herein may be employed to create entire genomes for introduction into host cells for the creation of entirely artificial designer living organisms.

In specific embodiments, the present invention provides a method for the synthesis of a replication-competent, double-stranded polynucleotide, wherein the polynucleotide comprises an origin of replication, a first coding region and a first regulatory element directing the expression of the first coding region.

Additionally the method may further comprise the step of amplifying the double-stranded polynucleotide. In specific embodiments, the double-stranded polynucleotide comprises 100, 200, 300, 400, 500, 600, 700, 800, 900, 1000, 5000, $10 \times 10^3$, $20 \times 10^3$, $30 \times 10^3$, $40 \times 10^3$, $50 \times 10^3$, $60 \times 10^3$, $70 \times 10^3$, $80 \times 10^3$, $90 \times 10^3$, $1 \times 10^4$, $1 \times 10^5$, $1 \times 10^6$, $1 \times 10^7$, $1 \times 10^8$, $1 \times 10^9$ or $1 \times 10^{10}$ base pairs in length. The first regulatory element may be a promoter. In certain embodiments, the double-stranded polynucleotide further comprises a second regulatory element, the second regulatory element being a polyadenylation signal. In yet further embodiments, the double-stranded polynucleotide comprises a plurality of coding regions and a plurality of regulatory elements. Specifically, it is contemplated that the coding regions encode products that comprise a biochemical pathway. In particular embodiments the biochemical pathway is glycolysis. More particularly, it is contemplated that the coding regions encode enzymes selected from the group consisting of hexokinase, phosphohexose isomerase, phosphofructokinase-1, aldolase, triose-phosphate isomerase, glyceraldehyde-3-phosphate dehydrogenase, phosphoglycerate kinase, phosphoglycerate mutase, enolase and pyruvate kinase enzymes of the glycolytic pathway.

In other embodiments, the biochemical pathway is lipid synthesis, cofactor synthesis. Particularly contemplated are synthesis of lipoic acid, riboflavin synthesis nucleotide synthesis. the nucleotide may be a purine or a pyrimidine.

In certain other embodiments it is contemplated that the coding regions encode enzymes involved in a cellular process selected from the group consisting of cell division, chaperone, detoxification, peptide secretion, energy metabolism, regulatory function, DNA replication, transcription, RNA processing and tRNA modification. In preferred embodiments, the energy metabolism is oxidative phosphorylation.

It is contemplated that the double-stranded polynucleotide is a DNA or an RNA. In preferred embodiments, the double-stranded polynucleotide may be a chromosome. The double-stranded polynucleotide may be an expression construct. Specifically, the expression construct may be a bacterial expression construct, a mammalian expression construct or a viral expression construct. In particular embodiments, the double-stranded polynucleotide comprises a genome selected from the group consisting of bacterial genome, yeast genome, viral genome, mammalian genome, amphibian genome and avian genome.

In those embodiments in which the genome is a viral genome, the viral genome may be selected from the group consisting of retrovirus, adenovirus, vaccinia virus, herpesvirus and adeno-associated virus.

The present invention further provides a method of producing a viral particle.

Another embodiment provides a method of producing an artificial genome, wherein the chromosome comprises all coding regions and regulatory elements found in a corresponding natural chromosome. In specific embodiments, the corresponding natural chromosome is a human mitochondrial genome. In other embodiments, the corresponding natural chromosome is a chloroplast genome.

Also provided is a method of producing an artificial genetic system, wherein the system comprises all coding regions and regulatory elements found in a corresponding natural biochemical pathway. Such a biochemical pathway will likely possess a group of enzymes that serially metabolize a compound. In particularly preferred embodiments, the biochemical pathway comprises the activities required for glycolysis. In other embodiments, the biochemical pathway comprises the enzymes required for electron transport. In still further embodiments, the biochemical pathway comprises the enzyme activities required for photosynthesis.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Flow diagram of the Jurassic Park paradigm for the reassembly of living organisms.

FIG. 2. Flow diagram of the strategy of synthetic genetics.

FIG. 4. Design of plasmid synlux4. The sequence of 4800 is annotated with the locations of lux A+B genes, neomycin/kanamycin phosphotransferase and pUC19 sequences.

FIG. 5. List of component oligonucleotides derived from the sequence of Synlux4 in FIG. 4.

FIG. 6. Schema for the combinatoric assembly of synthetic plasmids from component oligonucleotides.

FIG. 7. SynGene program for generating overlapping oligonucleotides sufficient to reassemble the gene or plasmid.

DESCRIPTION OF ILLUSTRATIVE EMBODIMENTS

Figure 3:
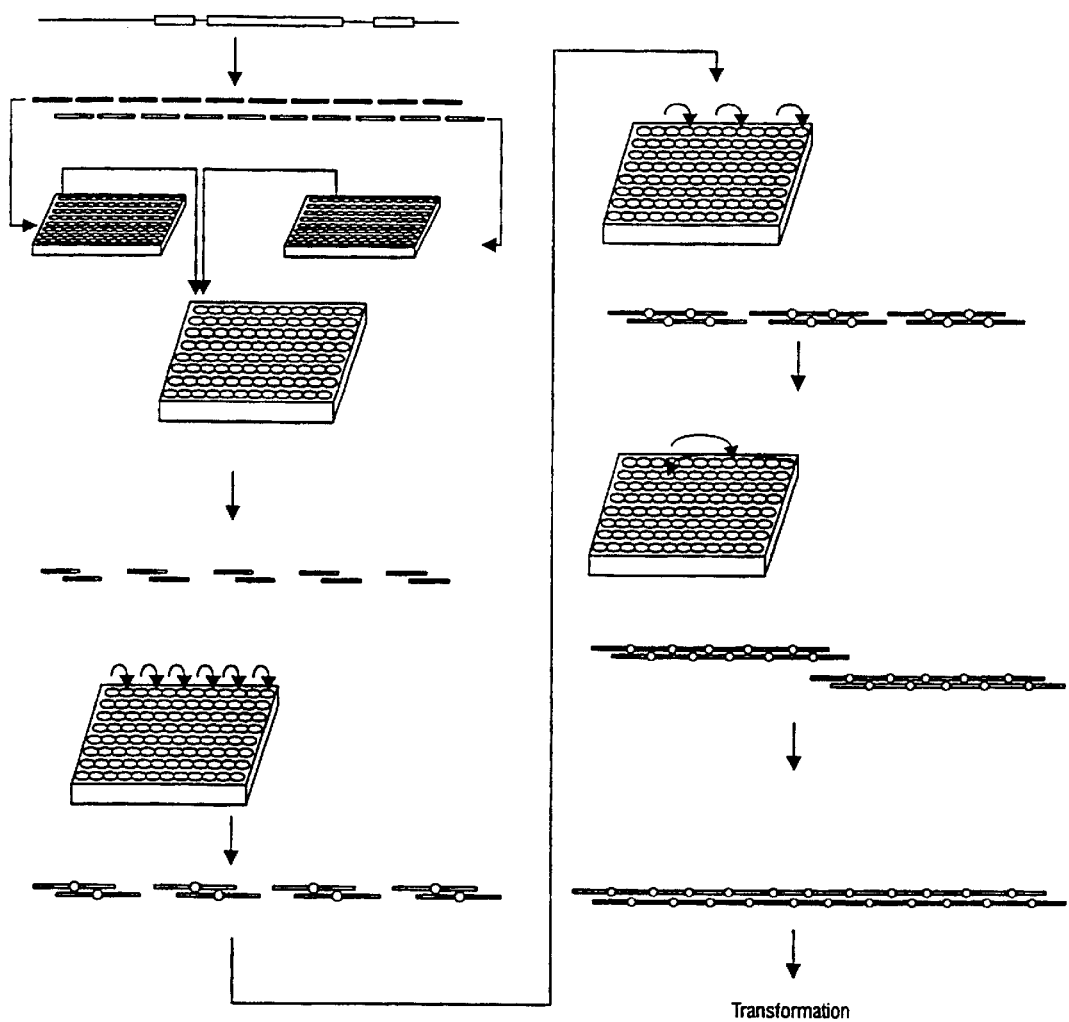
FIG. 3. Flow diagram of the strategy for combinatoric assembly of oligonucleotides into complete genes or genomes.

The complete sequence of complex genomes, including the human genome, make large scale functional approaches to genetics possible. The present invention outlines a novel approach to utilizing the results of genomic sequence information by computer directed gene synthesis based on computing on the human genome database. Specifically, the invention describes chemical synthesis and resynthesis of genes for transfer of these genes into a suitable host cells.

The present invention provides methods that can be used to synthesize de novo, DNA segments that encode sets of genes, either naturally occurring genes expressed from natural or artificial promoter constructs or artificial genes derived from synthetic DNA sequences, which encodes elements of biological systems that perform a specified function or attribution of an artificial organism as well as entire genomes. In producing such systems and genomes, the present invention provides the synthesis of a replication-competent, double-stranded polynucleotide, wherein the polynucleotide has an origin of replication, a first coding region and a first regulatory element directing the expression of the first coding region. By replication competent, it is meant that the polynucleotide is capable of directing its own replication. Thus, it is envisioned that the polynucleotide will possess all the cis-acting signals required to facilitate its own synthesis. In this respect, the polynucleotide will be similar to a plasmid or a virus, such that once placed within a cell, it is able to be replicated by a combination of the polynucleotide's and cellular functions.

Thus, using the techniques of the present invention, one of skill in the art can create an artificial genome that is capable of encoding all the activities required for sustaining its own existence. Also contemplated are artificial genetic systems that are capable of encoding enzymes and activities of a particular biochemical pathway. In such a system, it will be desirable to have all the activities present such that the whole biochemical pathway will operate. The co-expression of a set of enzymes required for a particular pathway constitutes a complete genetic or biological system. For example, the co-expression of the enzymes involved in glycolysis constitutes a complete genetic system for the production of energy in the form of ATP from glucose. Such systems for energy production may include groups of enzymes which naturally or artificially serially metabolize a set of compounds.

The types of biochemical pathways would include but are not limited to those for the biosynthesis of cofactors prosthetic groups and carriers (lipoate synthesis, riboflavin synthesis pyridine nucleotide synthesis); the biosynthesis of the cell envelopes (membranes, lipoproteins, porins, surface polysaccharides, lipopolysaccharides, antigens and surface structures); cellular processes including cell division, chaperones, detoxification, protein secretion, central intermediary metabolism (energy production vi phosphorus compounds and other); energy metabolism including aerobic, anaerobic, ATP proton motive force interconversions, electron transport, glycolysis triose phosphate pathway, pyruvate dehydrogenase, sugar metabolism; purine, pyrimidine nucleotide synthesis, including 2'deoxyribonucleotide synthesis, nucleotide and nucleoside interconversion, salvage of nucleoside and nucleotides, sugar-nucleotide biosynthesis and conversion; regulatory functions including transcriptional and translational controls, DNA replication including degradation of DNA, DNA replication, restriction modification, recombination and repair; transcription including degradation of DNA, DNA-dependent RNA polymerase and transcription factors; RNA processing; translation including amino acyl tRNA synthetases, degradation of peptides and glycopeptides, protein modification, ribosome synthesis and modification, tRNA modification; translation factors transport and binding proteins including amino acid, peptide, amine carbohydrate, organic alcohol, organic acid and cation transport; and other systems for the adaptation, specific function or survival of an artificial organism.

A. Definitions

DNA segment—a linear piece of DNA having a double-stranded region and both 5'- and 3'-ends; the segment may be of any length sufficiently long to be created by the hybridization of at least two oligonucleotides have complementary regions.

Oligonucleotides—small DNA segments, single-stranded or double-stranded, comprised of the nucleotide bases A, T, G and C linked through phosphate bonds; oligonucleotides typically range from about 10 to 100 base pairs.

Plus strand—by convention, the single-strand of a double-stranded DNA that starts with the 5' end to the left as one reads the sequence.

Minus strand—by convention, the single-strand of a double-stranded DNA that starts with the 3' end to the left as one reads the sequence.

Complementary—where two nucleic acids have at least a portion of their sequences, when read in opposite (5'→3'; 3'→5') direction, that pair sequential nucleotides in the following fashion: A-T, G-C, T-A, G-C.

Oligonucleotide sets—a plurality of oligonucleotides that, taken together, comprise the sequence of a plus or minus strand of a DNA segment.

Annealed products—two or more oligonucleotides having complementary regions, where they are permitted, under proper conditions, to base pair, thereby producing double stranded regions.

B. The Present Invention

The present invention describes methods for enabling the creation of DNA molecules, genomes and entire artificial living organisms based upon information only, without the requirement for existing genes, DNA molecules or genomes.

The methods of the present invention are diagrammed in FIG. 1 and FIG. 2 and generally involve the following steps. Generally, using simple computer software, comprising sets of gene parts and functional elements it is possible to construct a virtual polynucleotide in the computer. This polynucleotide consists of a string of DNA bases, G, A, T or C, comprising for example an entire artificial genome in a linear string. For transfer of the synthetic gene into for example, bacterial cells the polynucleotide should contain the sequence for a bacterial (such as pBR322) origin of replication. For transfer into eukaryotic cells, it should contain the origin of replication of a mammalian virus, chromosome or subcellular component such as mitochondria.

Following construction, simple computer software is then used to break down the genome sequence into a set of overlapping oligonucleotides of specified length. This results in a set of shorter DNA sequences which overlap to cover the entire genome in overlapping sets. Typically, a gene of 1000 bases pairs would be broken down into 20 100-mers where 10 of these comprise one strand and 10 of these comprise the other strand. They would be selected to overlap on each strand by 25 to 50 base pairs.

This step is followed by direction of chemical synthesis of each of the overlapping set of oligonucleotides using an array type synthesizer and phosphoamidite chemistry resulting in an array of synthesized oligomers. The next step is to balance concentration of each oligomer and pool the oligomers so that a single mixture contains equal concentrations of each. The mixed oligonucleotides are treated with T4 polynucleotide kinase to 5' phosphorylate the oligonucleotides. The next step is to carry out a "slow" annealing step to co-anneal all of the oligomers into the sequence of the predicted gene or genome. This is done by heating the mixture to 80° C., then allowing it to cool slowly to room temperature over several hours. The mixture of oligonucleotides is then treated with T4 DNA ligase (or alternatively topoisomerase) to join the oligonucleotides. The oligonucleotides are then transferred into competent host cells.

The above technique represents a "combinatorial" assembly strategy where all oligonucleotides are jointly co-annealed by temperature-based slow annealing. A variation on this strategy, which may be more suitable for very long genes or genomes, such as greater than 5,000 base pairs final length, is as follows. Using simple computer software, comprising sets of gene parts and functional elements, a virtual gene or genome is constructed in the computer. This gene or genome would consist of a string of DNA bases, G, A, T or C, comprising the entire genome in a linear string. For transfer of the synthetic gene into bacterial cells, it should contain the sequence for a bacterial (such as pBR322) origin of replication.

The next step is to carry out a ligation chain reaction using a new oligonucleotide addition each step. With this procedure, the first oligonucleotide in the chain is attached to a solid support (such as an agarose bead). The second is added along with DNA ligase, and annealing and ligation reaction carried out, and the beads are washed. The second, overlapping oligonucleotide from the opposite strand is added, annealed and ligation carried out. The third oligonucleotide is added and ligation carried out. This procedure is replicated until all oligonucleotides are added and ligated. This procedure is best carried out for long sequences using an automated device. The DNA sequence is removed from the solid support, a final ligation (is circular) is carried out, and the molecule transferred into host cells.

Alternatively, it is contemplated that if the ligation kinetics allow all the oligonucleotides may be placed in a mixture and ligation be allowed to proceed. In yet another embodiment, a series of smaller polynucleotides may be made by ligating 2, 3, 4, 5, 6, or 7 oligonucleotides into one sequence and adding this to another sequence comprising a similar number of oligonucleotides parts.

The ligase chain reaction ("LCR"), disclosed in EPO No. 320 308, is incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LAC for binding probe pairs to a target sequence. The following sections describe these methods in further detail.

C. Nucleic Acids

The present invention discloses the artificial synthesis of genes. In one embodiment of the present invention, the artificial genes can be transferred into cells to confer a particular function either as discrete units or as part of artificial chromosomes or genome. One will generally prefer to design oligonucleotides having stretches of 15 to 100 nucleotides, 25 to 200 nucleotides or even longer where desired. Such fragments may be readily prepared by, directly synthesizing the fragment by chemical means as described below.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of hybrization selectivity. Typically high selectivity is favored.

For applications requiring high selectivity, one typically will desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the oligonucleotide and the template or target strand. It generally is appreciated that conditions can be rendered more stringent by the addition of increasing amounts of formamide.

For certain applications, for example, by analogy to, substitution of nucleotides by site-directed mutagenesis, it is appreciated that lower stringency conditions may be used. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In certain embodiments, it will be advantageous to determining the hybridization of ilogonucleotides by employing as a label. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically,to identify whether specific hybridization with complementary oligonucleotidehas occured.

In embodiments involving a solid phase, for example the first oligonucleotide is adsorbed or otherwise affixed to a selected matrix or surface. This fixed, single-stranded nucleic acid is then subjected to hybridization with the complementary oligonucleotides under desired conditions. The selected conditions will also depend on the particular circumstances based on the particular criteria required (depending, for example, on the G+C content, type of target nucleic acid, source of nucleic acid, size of hybridization probe, etc.). Following washing of the hybridized surface to remove non-specifically bound oligonucleotides, the hybridization may be detected, or even quantified, by means of the label.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

The nucleic acids employed may encode antisense constructs that hybridize, under intracellular conditions, to a nucleic acid of interest. The term "antisense construct" is intended to refer to nucleic acids, preferably oligonucleotides, that are complementary to the base sequences of a target DNA. Antisense oligonucleotides, when introduced into a target cell, specifically bind to their target nucleic acid and interfere with transcription, RNA processing, transport, translation and/or stability. Antisense constructs may be designed to bind to the promoter and other control regions, exons, introns or even exon-intron boundaries of a gene.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

According to the present invention, DNA segments of a variety of sizes will be produced. These DNA segments will, by definition, be linear molecules. As such, they typically will be modified before further use. These modifications include, in one embodiment, the restriction of the segments to produce one or more "sticky ends" compatible with complementary ends of other molecules, including those in vectors capable of supporting the replication of the DNA segment. This manipulation facilitates "cloning" of the segments.

Typically, cloning involves the use of restriction endonucleases, which cleave at particular sites within DNA strands, to prepare a DNA segment for transfer into a cloning vehicle. Ligation of the compatible ends (which include blunt ends) using a DNA ligase completes the reaction. Depending on the situation, the cloning vehicle may comprises a relatively small portion of DNA, compared to the insert. Alternatively, the cloning vehicle may be extremely complex and include a variety of features that will affect the replication and function of the DNA segment. In certain embodiments, a rare cutter site may be introduced into the end of the polynucleotide sequence.

Cloning vehicles include plasmids such as the pUC series, Bluescript™ vectors and a variety of other vehicles with multipurpose cloning sites, selectable markers and origins of replication. Because of the nature of the present invention, the cloning vehicles may include such complex molecules as phagemids and cosmids, which hold relatively large pieces of DNA. In addition, the generation of artificial chromosomes, and even genomes.

Following cloning into a suitable vector, the construct then is transferred into a compatible host cell. A variety of different gene transfer techniques are described elsewhere in this document. Culture of the host cells for the intended purpose (amplification, expression, subcloning) follows.

Throughout this application, the term "expression construct" is meant to include a particular kind of cloning vehicle containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV. Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. It is envisioned that any elements/promoters may be employed in the context of the present invention. Below is a list of viral promoters, cellular promoters/enhancers and inducible promoters/enhancers that could be used in combination with the nucleic acid encoding a gene of interest in an expression construct. Enhancer/promoter elements contemplated for use with the present invention include but are not limited to Immunoglobulin Heavy Chain, Immunoglobulin Light, Chain T-Cell Receptor, HLA DQ α and DQ β, β-Interferon, Interleukin-2, Interleukin-2 Receptor, MHC Class II 5, MHC Class II HLA-DRα, β-Actin, Muscle Creatine Kinase, Prealbumin (Transthyretin), Elastase I, Metallothionein, Collagenase, Albumin Gene, α-Fetoprotein, τ-Globin, β-Globin, e-fos, c-HA-ras, Insulin, Neural Cell Adhesion Molecule (NCAM), α1-Antitrypsin, H2B (TH2B) Histone, Mouse or Type I Collagen, Glucose-Regulated Proteins (GRP94 and GRP78), Rat Growth Hormone, Human Serum Amyloid A (SAA), Troponin I (TN I), Platelet-Derived Growth Factor, Duchenne Muscular Dystrophy, SV40, Polyoma, Retroviruses, Papilloma Virus, Hepatitis B Virus, Human Immunodeficiency Virus, Cytomegalovirus, Gibbon Ape Leukemia Virus. Inducible promoter elements and, their associated inducers are listed in Table 2 below. This list is not intended to be exhaustive of all the possible elements involved in the promotion of transgene expression but, merely, to be exemplary thereof. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

TABLE 2

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), H$_2$O$_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

Use of the baculovirus system will involve high level expression from the powerful polyhedron promoter.

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In certain embodiments, it may be desirable to include specialized regions known as telomeres at the end of a genome sequence. Telomeres are repeated sequences found at chromosome ends and it has long been known that chromosomes with truncated ends are unstable, tend to fuse with other chromosomes and are otherwise lost during cell division. Some data suggest that telomeres interaction the nucleoprotein complex and the nuclear matrix. One putative role for telomeres includes stabilizing chromosomes and shielding the ends from degradative enzyme.

Another possible role for telomeres is in replication. According to present doctrine, replication of DNA requires starts from short RNA primers annealed to the 3'-end of the template. The result of this mechanism is an "end replication problem" in which the region corresponding to the RNA primer is not replicated. Over many cell divisions, this will result in he progressive truncation of the chromosome. It is thought that telomeres may provide a buffer against this effect, at least until they are themselves eliminated by this effect. A further structure to be included in DNA segments is a centromere.

In certain embodiments of the invention, the delivery of a nucleic acid in a cell may be identified in vitro or in vivo by including a marker in the expression construct. The marker would result in an identifiable change to the transfected cell permitting easy identification of expression.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk⁻, hgprt⁻ or aprt⁻ cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin.

Usually the inclusion of a drug selection marker aids in cloning and in the selection of transformants, for example, neomycin, puromycin, hygromycin, DHFR, GPT, zeocin and histidinol. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

D. Encoded Proteins

In this application, the inventors use genetic information for creative or synthetic purposes. The complete genome sequence will give a catalog of all genes necessary for the survival, reproduction, evolution and speciation of an organisms and, given suitable high tech tools, the genomic information may be modified or even created from "scratch" in order to synthesize life. Thus it is contemplated that a combination of suitable energy generation genes, regulatory genes, and other functional genes could be constructed which would be sufficient to render an artificial organism with the basic functionalities to enable independent survival.

To meet this goal, the present invention utilizes known cDNA sequences for any given gene to express proteins in an artificial organism. Any protein so expressed in this invention may be modified for particular purposes according to methods well known to those of skill in the art. For example, particular peptide residues may be derivatized or chemically modified in order to alter the immune response or to permit coupling of the peptide to other agents. It also is possible to change particular amino acids within the peptides without disturbing the overall structure or antigenicity of the peptide. Such changes are therefore termed "conservative" changes and tend to rely on the hydrophilicity or polarity of the residue. The size and/or charge of the side chains also are relevant factors in determining which substitutions are conservative.

Once the entire coding sequence of a gene has been determined, the gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

Examples of expression systems known to the skilled practitioner in the art include bacteria such as *E. coli,* yeast such as *Saccharomyces cerevisia* and *Pichia pastoris,* baculovirus, and mammalian expression systems such as in COS or CHO cells. In one embodiment, polypeptides are expressed in *E. coli* and in baculovirus expression systems. A complete gene can be expressed or, alternatively, fragments of the gene encoding portions of polypeptide can be produced.

In one embodiment, the gene sequence encoding the polypeptide is analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli,* as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Therefore, antibodies to these sequences will not prove useful for in vivo or in situ studies. Deletion of transmembrane-encoding sequences from the genes used for expression can be achieved by standard techniques. For example, fortuitously-placed restriction enzyme sites can be used to excise the desired gene fragment, or PCR™-type amplification can be used to amplify only the desired part of the gene. The skilled practitioner will realize that such changes must be designed so as not to change the translational reading frame for downstream portions of the protein-encoding sequence.

In one embodiment, computer sequence analysis is used to determine the location of the predicted major antigenic determinant epitopes of the polypeptide. Software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

Once this analysis is made, polypeptides can be prepared that contain at least the essential features of the antigenic determinant and that can be employed in the generation of antisera against the polypeptide. Minigenes or gene fusions encoding these determinants can be constructed and inserted into expression vectors by standard methods, for example, using PCR™ methodology.

The gene or gene fragment encoding a polypeptide can be inserted into an expression vector by standard subcloning techniques. In one embodiment, an *E. coli* expression vector is used that produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.). Some of these systems produce recombinant polypeptides bearing only a small number of additional amino acids, which are unlikely to affect the antigenic ability of the recombinant polypeptide. For example, both the FLAG system and the 6xHis system add only short sequences, both of that are known to be poorly antigenic and which do not adversely affect folding of the polypeptide to its native conformation. Other fission systems produce polypeptide where it is desirable to excise the fusion partner from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Recombinant bacterial cells, for example *E. coli,* are grown in any of a number of suitable media, for example LB, and the expression of the recombinant polypeptide induced by adding IPTG to the media or switching incubation to a higher temperature. After culturing the bacteria for a further period of between 2 and 24 h, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

In another embodiment, the expression system used is one driven by the baculovirus polyhedron promoter. The gene encoding the polypeptide can be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al., A MANUAL OF METHODS FOR BACULOVIRUS VECTORS AND INSECT CELL CULTURE PROCEDURES, Texas Agricultural Experimental Station.

In designing a gene that encodes a particular polypeptide, the hydropathic index of amino acids may be considered. Table 3 provides a codon table showing the nucleic acids that encode a particular amino acid. The importance of the hydropathic amino acid index in conferring interactive biologic function on a protein is generally understood in the art (Kyte & Doolittle, 1982). The following is a brief discussion of the the hydropathic amino acid index for use in the present invention.

TABLE 3

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |

TABLE 3-continued

| Amino Acids | | | Codons | | | | | |
|---|---|---|---|---|---|---|---|---|
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

E. Expression of and Delivery of Genes

I. Expression

Once the designer gene, genome or biological system has been made. according the methods described herein, the polynucleotides can be expressed as encoded peptides or proteins of the gene, genome or biological system. The engineering of the polynucleotides for expression in a prokaryotic or eukaryotic system may be performed by techniques generally known to those of skill in recombinant expression. Therefore, promoters and other elements specific to a bacterial mammalian or other system may be encluded in the polynucleotide sequence. It is believed that virtually any expression system may be employed in the expression of the claimed nucleic acid sequences.

The artificially generated polynucleotide sequences are suitable for eukaryotic expression, as the host cell will generally process the genomic transcripts to yield functional mRNA for translation into protein. It is believed that the use of a designer gene version will provide advantages in that the size of the gene will generally be much smaller and more readily employed to transfect the targeted cell than will a genomic gene, which will typically be up to an order of magnitude larger than the designer gene. However, the inventor does not exclude the possibility of employing a genomic version of a particular gene where desired.

As used herein, the terms "engineered" and "recombinant" cells are intended to refer to a cell into which an exogenous polynucleotide described herein has been introduced. Therefore, engineered cells are distinguishable from naturally-occurring cells which do not contain a recombinantly introduced exogenous polynucleotide. Engineered cells are thus cells having a gene or genes introduced through the hand of man. Recombinant cells include those having an introduced polynucleotides, and also include polynucleotides positioned adjacent to a promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant phage DNA, plasmid DNA or cosmid DNA expression vectors.

Certain examples of prokaryotic hosts are E. coli strain RR1, E. coli LE392, E. coli B, E. coli χ 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is often transformed using pBR322, a plasmid derived from an E. coli species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as E. coli LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid contains the trpl gene, which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g. cauliflower mosaic virus, CaMV; tobacco mosaic virus, TMV) or transformed with recombinant plasmid expression vectors (e.g., Ti plasmid) containing one or more coding sequences.

In a useful insect system, Autograph californica nuclear polyhidrosis virus (AcNPV) is used as a vector to express foreign genes. The virus grows in Spodoptera frugiperda cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed (e.g., U.S. Pat. No. 4,215,051).

Examples of useful mammalian host cell lines are VERO and HeLa cells, Chinese hamster ovary (CHO) cell lines, WI38, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

It is contemplated that the nucleic acids of the invention may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

II. Delivery

In various embodiments of the invention, the expression construct may comprise a virus or engineered construct derived from a viral genome. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario. Herpes simplex virus (HSV) is another attractive candidate, especially where neurotropism is desired. HSV also is relatively easy to manipulate and can be grown to high titers. Thus, delivery is less of a problem, both in terms of volumes needed to attain sufficient MOI and in a lessened need for repeat dosings.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang etal., 1991).

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al., (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct or DNA segment into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the DNA segment or expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes.

In certain embodiments, gene transfer may more easily be performed under ex vivo conditions. Ex vivo gene therapy refers to the isolation of cells from an organism, the delivery of a nucleic acid into the cells in vitro, and then the return of the modified cells back into an organism. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

F. Oligonucleotide Synthesis

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Phosphoramidite chemistry (Beaucage, and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Tetrazole is commonly used for the activation of the nucleoside phosphoramidite monomers. Tetrazole has an acidic proton which presumably protonates the basic nitrogen of the diisopropylamino phosphine group, thus making the diisopropylamino group a leaving group. The negatively charged tetrazolium ion then makes an attack on the trivalent phosphorous, forming a transient phosphorous tetrazolide species. The 5'-OH group of the solid support bound nucleoside then attacks the active trivalent phosphorous species, resulting in the formation of the internucleotide linkage. The trivalent phosphorous is finally oxidized to the pentavalent phosphorous. The US patents listed above describe other activators and solid supports for oligonucleotide synthesis.

High throughput oligonucleotide synthesis can be achieved using a synthesizer. The Genome Science and Technology Center, as one aspect of the automation development effort, recently developed a high throughput large scale oligonucleotide synthesizer. This instrument, denoted the MERMADE, is based on a 96-well plate format and uses robotic control to carry out parallel synthesis on 192 samples (2 96-well plates). This device has been variously described in the literature and in presentations, is generally available in the public domain (licensed from the University of Texas and available on contract from Avantec). The device has gone through various generations with differing operating parameters.

The device may be used to synthesize 192 oligonucleotides simultaneously with 99% success. It has virtually 100% success for oligomers less than 60 bp; operates at 20 mM synthesis levels, and gives a product yield of >99% complete synthesis. Using these systems the inventor has synthesized over 10,000 oligomers used for sequencing, PCR™ amplification and recombinant DNA applications. For most uses, including cloning, synthesis success is sufficient such that post synthesis purification is not required.

Once the genome has been synthesized using the methods of the present invention it may be necessary to screen the sequences for analysis of function. Specifically contemplated by the present inventor are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

The use of combinatorial synthesis and high throughput screening assays are well known to those of skill in the art, e.g. U.S. Pat. Nos. 5,807,754; 5,807,683; 5,804,563; 5,789,162; 5,783,384; 5,770,358; 5,759,779; 5,747,334; 5,686,242; 5,198,346; 5,738,996; 5,733,743; 5,714,320; 5,663,046 (each specifically incorporated herein by reference). These patents teach various aspects of the methods and compositions involved in the assembly and activity analyses of high density arrays of different polysubunits (polynucleotides or polypeptides). As such it is contemplated that the methods and compositions described in the patents listed above may be useful in assay the activity profiles of the compositions of the present invention.

The present invention produces a replication competent polynucleotide. Viruses are naturally occurring replication competent pieces of DNA, to the extent that disclosure regarding viruses may be useful in the context of the present invention, the following is a disclosure of viruses. Researchers note that viruses have evolved to be able to deliver their DNA to various host tissues despite the human body's various defensive mechanisms. For this reason, numerous viral vectors have been designed by researchers seeking to create vehicles for therapeutic gene delivery. Some of the types of viruses that have been engineered are listed below.

II. Adenovirus

Adenovirus is a 36 kB, linear, double-strained DNA virus that allows substitution of large pieces of adenoviral DNA with foreign sequences up to 7 kB (Grunhaus and Horwitz, 1992). Adenovirus DNA does not integrate into the host cell chromosomal because adenoviral DNA can replicate in an episomal manner. Also, adenoviruses are structurally stable, and no genome rearrangement has been detected after extensive amplification. Adenovirus can infect virtually all epithelial cells regardless of their cell cycle stage. This means that adenovirus can infect non-dividing cells. So far, adenoviral infection appears to be linked only to mild disease such as acute respiratory disease in humans. This group of viruses can be obtained in high titers, e.g., $10^9$–$10^{11}$ plaque-forming units per ml, and they are highly infective.

Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

The E3 region encodes proteins that appears to be necessary for efficient lysis of Ad infected cells as well as preventing TNF-mediated cytolysis and CTL mediated lysis of infected cells. In general, the E4 region encodes is believed to encode seven proteins, some of which activate the E2 promoter. It has been shown to block host mRNA transport and enhance transport of viral RNA to cytoplasm. Further the E4 product is in part responsible for the decrease in early gene expression seen late in infection. E4 also inhibits E1A and E4 (but not E1B) expression during lytic growth. Some E4 proteins are necessary for efficient DNA replication however the mechanism for this involvement is unknown. E4 is also involved in post-transcriptional events in viral late gene expression; ie., alternative splicing of the tripartite leader in lytic growth. Nevertheless, E4 functions are not absolutely required for DNA replication but their lack will delay replication. Other functions include negative regulation of viral DNA synthesis, induction of sub-nuclear reorganization normally seen during adenovirus infection, and other functions that are necessary for viral replication, late viral mRNA accumulation, and host cell transcriptional shut off.

II. Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed ψ components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration requires the division of host cells (Paskind et al., 1975).

The retrovirus family includes the subfamilies of the oncoviruses, the lentiviruses and the spumaviruses. Two oncoviruses are Moloney murine leukemia virus (MMLV) and feline leukemia virus (FeLV). The lentiviruses include human immunodeficiency virus (HIV), simian immunodeficiency virus (SIV) and feline immunodeficiency virus (FIV). Among the murine viruses such as MMLV there is a further classification. Murine viruses may be ecotropic, xenotropic, polytropic or amphotropic. Each class of viruses target different cell surface receptors in order to initiate infection.

Further advances in retroviral vector design and concentration methods have allowed production of amphotropic and xenotropic viruses with titers of $10^8$ to $10^9$ cfu/ml (Bowles et al., 1996; Irwin et al, 1994; Jolly, 1994; Kitten et al., 1997).

Replication defective recombinant retroviruses are not acute pathogens in primates (Chowdhury et al., 1991). They have been successfully applied in cell culture systems to transfer the CFTR gene and generate cAMP-activated Cl⁻ secretion in a variety of cell types including human airway epithelia (Drumm et al., 1990, Olsen et al., 1992; Anderson et al., 1991; Olsen et al., 1993). While there is evidence of immune responses to the viral gag and env proteins, this does not prevent successful readministration of vector (McCormack et al., 1997). Further, since recombinant retroviruses have no expressed gene products other than the transgene, the risk of a host inflammatory response due to viral protein expression is limited (McCormack et al., 1997). As for the concern about insertional mutagenesis, to date there are no examples of insertional mutagenesis arising from any human trial with recombinant retroviral vectors.

More recently, hybrid lentivirus vectors have been described combining elements of human immunodeficiency virus (HIV) (Naldini et al., 1996) or feline immunodeficiency virus (FIV) (Poeschla et al., 1998) and MMLV. These vectors transduce nondividing cells in the CNS (Naldini et al., 1996; Blomer et al., 1997), liver (Kafri et al., 1997), muscle (Kafri et al., 1997) and retina (Miyoshi et al., 1997). However, a recent report in xenograft models of human airway epithelia suggests that in well-differentiated epithelia, gene transfer with VSV-G pseudotyped HIV-based lentivirus is inefficient (Goldman et al., 1997).

III. Adeno-Associated Virus

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et al., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Bertran et al., 1996; Kearns et al., 1996; Ponnazhagan et al., 1997a). Until recently, AAV was believed to infect almost all cell types, and even cross species barriers. However, it now has been determined that AAV infection is receptor-mediated (Ponnazhagan et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by Srivastava et al. (1983), and in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

IV. Vaccinia Virus

Vaccinia viruses are a genus of the poxvirus family. Vaccinia virus vectors have been used extensively because of the ease of their construction, relatively high levels of expression obtained, wide host range and large capacity for carrying DNA. Vaccinia contains a linear, double-stranded DNA genome of about 186 kB that exhibits a marked "A-T" preference. Inverted terminal repeats of about 10.5 kB flank the genome. The majority of essential genes appear to map within the central region, which is most highly conserved among poxviruses. Estimated open reading frames in vaccinia virus number from 150 to 200. Although both strands are coding, extensive overlap of reading frames is not common. U.S. Pat. No. 5,656,465 (specifically incorporated by reference) describes in vivo gene delivery using pox viruses.

V. Papovavirus

The papovavirus family includes the papillomaviruses and the polyomaviruses. The polyomaviruses include Simian Virus 40 (SV40), polyoma virus and the human polyomaviruses BKV and JCV. Papillomaviruses include the bovine and human papillomaviruses. The genomes of polyomaviruses are circular DNAs of a little more than 5000 bases. The predominant gene products are three virion proteins (VP1-3) and Large T and Small T antigens. Some have an additional structural protein, the agnoprotein, and others have a Middle T antigen. Papillomaviruses are somewhat larger, approaching 8 kB Little is known about the cellular receptors for polyomaviruses, but polyoma infection can be blocked by treating with sialidase. SV40 will still infect sialidase-treated cells, but JCV cannot hemagglutinate cells treated with sialidase. Because interaction of polyoma VP1 with the cell surface activates c-myc and c-fos, it has been hypothesized that the virus receptor may have some properties of a growth factor receptor. Papillomaviruses are specifically tropic for squamous epithelia, though the specific receptor has not been identified.

VI. Paramyxovirus

The paramyxovirus family is divided into three genera: paramyxovirus, morbillivirus and pneumovirus. The paramyxovirus genus includes the mumps virus and Sendai virus, among others, while the morbilliviruses include the measles virus and the pneumoviruses include respiratory syncytial virus (RSV). Paramyxovirus genomes are RNA based and contain a set of six or more genes, covalently linked in tandem. The genome is something over 15 kB in length. The viral particle is 150–250 nm in diameter, with "fuzzy" projections or spikes protruding therefrom. These are viral glycoproteins that help mediate attachment and entry of the virus into host cells.

A specialized series of proteins are involved in the binding an entry of paramyxoviruses. Attachment in Paramyxoviruses and Morbilliviruses is mediated by glycoproteins that bind to sialic acid-containing receptors. Other proteins anchor the virus by embedding hydrophobic regions in the lipid bilayer of the cell's surface, and exhibit hemagluttinating and neuraminidase activities. In Pnemoviruses, the glycoproptein is heavily glycosylated with O-glycosidic bonds. This molecule lacks the exhibit hemagluttinating and neuraminidase activities of its relatives.

VII. Herpesvirus

Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizrnan, 1974; Honess and Roizman 1975; Roizman and Sears, 1995). The expression of a genes, the first set of genes to be expressed after infection, is enhanced by the virion protein number 16, or α-transducing factor (Post et al., 1981; Batterson and Roizman, 1983; Campbell et al., 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Combinatoric Gene Assembly

The inventor has developed a strategy of oligomer assembly into larger DNA molecules denoted combinatoric assembly. The procedure is carried out as follows: one may design a plasmid using one of a number of commercial or public domain computer programs to contain the genes, promoters, drug selection, origin of replication, etc. required. SynGene v.2.0 is a program that generates a list of overlapping oligonucleotides sufficient to reassemble the gene or plasmid (see FIG. 7). For instance, for a 5000 bp gene, SynGene 2.0 can generate two lists of 100 component 50 mers from one strand and 100 component 50 mers from the complementary strand such that each pair of oligomers will overlap by 25 base pairs. The program checks the sequence for repeats and produces a MERMADE input file which directly programs the oligonucleotide synthesizer. The synthesizer produces two sets of 96-well plates containing the complementary oligonucleotides. A SynGene program is depicted in FIG. 7. This program is designed to break down a designer gene or genome into oligonucleotides fore synthesis. The program is for the complete synthetic designer gene and is based upon an original program for formatting DNA sequences written by Dr. Glen Evans.

Combinatoric assembly is best carried out using a programmable robotic workstation such as a Beckman Biomek 2000. In short, pairs of oligomers which overlap are mixed and annealed. Following annealing, a smaller set of duplex oligomers is generated. These are again paired and annealed, forming a smaller set of larger oligomers. Sequentially, overlapping oligomers are allowed to anneal until the entire reassembly is completed. Annealing may be carried out in the absence of ligase, or each step may be followed by ligation. In one configuration, oligomers are annealed in the presence of topoisomerase 2, which does not require 5' phosphorylation of the oligomer, occurs at room temperature, and is a rapid (5 minute) reaction as opposed to 12 h ligation at 12°. Following the complete assembly, the resulting DNA molecule can be used for its designed purpose, usually transformation into a bacterial host for replication. The steps in this cycle are outlined in FIG. 3.

This approach has a major advantage over traditional recombinant DNA based cloning. While it is technically feasible to make virtually any modification or mutation in existing DNA molecules, the effort required, as will as the high technical skill, make some constructions difficult or tedious. This method, while having been used for many years, is not applicable to automated gene cloning or large scale creation or entirely novel DNA sequences.

Example 2

Production of Artificial Genes

In one example, the present invention will produce a known gene of about 1000 base pairs in length by the following method. A set of oligonucleotides, each of 50 bases, is generated such that the entire plus strand of the gene is represented. A second set of oligonucleotides, also comprised of 50-mers, is generated for the minus strand. This set is designed, however, such that complementary pairing with the first and second sets results in overlap of "paired" sequences, i.e., each oligonucleotide of the first set is complementary with regions from two oligonucleotides of the second set (with the possible exception of the terminal oligonucleotides). The region of overlap is set at 30 bases, leaving a 20 base pair overhang for each pair. The first and said second set of oligonucleotides is annealed in a single mixture and treated with a ligating enzyme.

In another example, the gene to be synthesized is about 5000 base pairs. Each set of oligonucleotides is made up of fifty 100-mers with overlapping regions, of complementary oligonucleotides, of 75 bases, leaving 25 base "sticky ends." In this embodiment, the 5' terminal oligonucleotide of the first oligonucleotide set is annealed with the 3' terminal oligonucleotide of the second set to form a first annealed product, then the next most 5' terminal oligonucleotide of the first set is annealed with the first annealed product to form a second annealed product, and the process is repeated until all oligonucleotides of said first and said second sets have been annealed. Ligation of the products may occur between steps or at the conclusion of all hybridizations.

In a third example, a gene of 100,000 bp is synthesize from one thousand 100-mers. Again, the overlap between "pairs" of plus and minus oligonucleotides is 75 bases, leaving a 25 base pair overhang. In this method, a combinatorial approach is used where corresponding pairs of partially complementary oligonucleotides are hybridized in first step. A second round of hybridization then is undertaken with appropriately complementary pairs of products from the first round. This process is repeated a total of 10 times, each round of hybridization reducing the number of products by half. Ligation of the products then is performed.

Example 3

Large Scale Expression of Human Gene Products

Once the human genome has been characterized, functional analysis of the human genome, based upon the complete sequence, will require a variety of approaches to structural, functional and network biology. The approach proposed herein for producing a series of expression constructs representing all potential human gene products and the assembly of sets of bacterial and/or yeast expressing these products will provide an important avenue into the beginnings of functional analysis.

Secondly, the approach described here, when developed to its theoretical optima, will allow the large scale transfer of genes to cell lines or organisms for functional analysis. The long term goal of this concept is the creation of living organisms entirely based on bioinformatics and information processing. Obviously, the knowledge of the complete sequence is not sufficient to appreciate the myriad of biological concepts inherent in life.

Example 4

Construction of a Synthetic Plasmid

A DNA molecule was designed using synthetic parts of previously known plasmids. As a demonstration of this technique, plasmid synlux4 was designed. Synlux4 consists of 4800 base pairs of DNA. Within this sequence are included the sequence of lux A and lx B, the A and B components of the luciferase protein from Vibrio Fisheri, potions of plasmid pUC19 including the origin of replication and replication stability sequences, the promoter and coding sequence for tn9 kanamnycin/neomycin phosphotransferase. The sequence was designed on a computer using Microsoft Word and Vector NTI (InforMax, Inc.). The sequence is listed in FIG. 4.

Following design, a computer program SynGene 2.0 was used to break the sequence down into components consisting of overlapping 50-mer oligonucleotides. From the 4800 base pair sequence, 192 50-mers were designed. The component oligonucleotides are listed in FIG. 5. These component oligonucleotides were synthesized using a custom 96-well oligonucleotide synthesizer (Rayner, et al.) Genome Research, 8, 741–747 (1998). The component oligonucleotides were produced in two 96-well microtitre plates, each plate holding one set of component oligonucleotides. Thus, plate one held the forward strand oligos and plate 2 held the reverse strand oligos.

The oligonucleotides were assembled and ligations carried out using a Biomek 1000 robotic workstation (Beckman). Sequential transfers of oligonucleotides were done by pipetting from one well to a second well of the plate and a ligation reaction carried out using T4 ligase. The pattern of assembly is delineated in FIG. 6.

Following assembly, the resulting ligation mix was used to transform competent E. coli strain DH5a. The transformation mix was plated on LB plates containing 25 $\mu$g/ml kanamycin sulfate. and recombinant colonies obtained. The resulting recombinant clones were isolated, cloned, and DNA prepared. The DNA was analyzed on 1% agarose gels in order detect recombinant molecules. Clones were shown to contain the expected 4800 base pair plasmid containing lux A and B genes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson et al. U.S. Pat. No. 5,399,346, 1995.
Anderson et al., *Science*, 253:202–205, 1991.
Baichwal and Sugden, "Vectors for gene transfer derived from animal DNA viruses: Transient and stable expression of transferred genes," In: *Gene Transfer,* Kucherlapati (ed.), New York, Plenum Press, pp. 117–148, 1986.
Battersonand Roizman, *J. Virol.,* 46:371–377, 1983.
Beaucage, and Lyer, *Tetrahedron,* 48:2223–2311, 1992
Benvenisty and Neshif, "Direction introduction of genes into rats and expression of the genes," *Proc. Nat. Acad. Sci. USA,* 83:9551–9555, 1986.
Berns and Bohenzky, *Adv. Virus Res.,* 32:243–307, 1987.
Bertran, et al., *J Virol.,* 70(10):6759–6766, 1996.
Bittner et al., *Methods in Enzymol,* 153:516–544, 1987.
Blomer et al., Highly efficient and sustained gene transfer in adult neurons with a lentivirus vector. *J. Virol.* 71:6641–6649, 1997
Bowles et al., *Hum. Gene Ther.,* 7:1735–1742, 1996.
Chang et al., "Foreign gene delivery and expression in hepatocytes using a hepatitis B virus vector," *Hepatology,* 14:124A, 1991.
Chen and Okayama, "High-efficiency transfection of mammalian cells by plasmid DNA," *Mol. Cell Biol.,* 7:2745–2752, 1987.
Coffin, "Retroviridae and their replication," In: *Virology,* Fields, Knipe (ed.), New York: Raven Press, pp. 1437–1500, 1990.
Coffin, In: *Virology,* ed., New York: Raven Press, pp. 1437–1500, 1990.
Colberre-Garapin et al., *J. Mol. Biol.,* 150:1, 1981.
Couch et al., "Immunization with types 4 and 7 adenovirus by selective infection of the intestinal tract," *Am. Rev. Resp. Dis.,* 88:394–403, 1963.
Coupar et al., "A general method for the construction of recombinant vaccinia virus expressing multiple foreign genes," *Gene,* 68:1–10, 1988.
Davey et al., EPO No. 329 822.
DeLuca et al., *J. Virol.,* 56:558–570, 1985.
Drumm et al., *Cell,* 62:1227–1233, 1990.
Dubensky et al., "Direct transfection of viral and plasmid DNA into the liver or spleen of mice," *Proc. Nat. Acad. Sci. USA,* 81:7529–7533, 1984.
Fechheimer et al., "Transfection of mammalian cells with plasmid DNA by scrape loading and sonication loading," *Proc. Natl. Acad. Sci. USA,* 84:8463–8467, 1987.
Ferkol et al., "Regulation of the phosphoenolpyruvate carboxykinase/human factor IX gene introduced into the livers of adult rats by receptor-mediated gene transfer," *FASEB J.,* 7:1081–1091, 1993.
Fraley et al., "Entrapment of a bacterial plasmid in phospholipid vesicles: Potential for gene transfer," *Proc. Natl. Acad. Sci. USA,* 76:3348–3352, 1979.
Freifelder, *Physical Biochemistry Applications to Biochemistry and Molecular Biology,* 2nd ed. Wm. Freeman and Co., New York, N.Y., 1982.
Friedmann, "Progress toward human gene therapy," *Science,* 244:1275–1281, 1989.
Frohman, In: *PCR™ Protocols: A Guide To Methods And Applications,* Academic Press, N.Y., 1990.
Ghosh-Choudhury et al., *EMBO J.,* 6:1733–1739, 1987.
Ghosh and Bachhawat, "Targeting of liposomes to hepatocytes," In: *Liver diseases, targeted diagnosis and therapy using specific receptors and ligands,* Wu, Wu (ed.), New York:, Marcel Dekker, pp. 87–104, 1991.
Gingeras et al., PCT Application WO 88/10315.
Glorioso et al., *Ann. Rev. Microbiol,* 49:675–710, 1995.
Goldman et al., *Hum Gene Ther.* 8(18): 2261–2268, 1997.
Gomez-Foix et al., "Adenovirus-mediated transfer of the muscle glycogen phosphorylase gene into hepatocytes confers altered regulation of glycogen," *J. Biol. Chem.,* 267:25129–25134, 1992.
Gopal, "Gene transfer method for transient gene expression, stable transfection, and cotransfection of suspension cell cultures," *Mol. Cell Biol.,* 5:1188–1190, 1985.
Graham and Prevec, "Adenovirus-based expression vectors and recombinant vaccines," *Biotech.,* 20:363–390, 1992.
Graham and Prevec, "Manipulation of adenovirus vector," In: *Methods in Molecular Biology: Gene Transfer and Expression Protocol,* Clifton and Murray (ed.), NJ, Humana Press, 7:109–128, 1991.
Graham and Van Der Eb, "A new technique for the assay of infectivity of human adenovirus 5 DNA," *Virology,* 52:456–467, 1973.
Graham et al., "Characteristics of a human cell line transformed by DNA from human adenovirus type 5," *J. Gen. Virol.,* 36:59–72, 1977.
Grunhaus and Horwitz, "Adenovirus as cloning vector," *Seminar in Virology,* 3:237–252, 1992.
Harland and Weintraub, "Translation of mammalian mRNA injected into Xenopus oocytes is specifically inhibitedby antisense RNA," *J. Cell Biol.,* 101:1094–1099, 1985.
Hermonat and Muzycska, "Use of adenoassociated virus as a mammalian DNA cloning vector: Transduction of neomycin resistance into mammalian tissue culture cells," *Proc. Nat. Acad. Sci. USA,* 81:6466–6470, 1984.
Hersdorffer et al., "Efficient gene transfer in live mice using a unique retroviral packaging line," *DNA Cell Biol.,* 9:713–723, 1990.
Herz and Gerard, "Adenovirus-mediated transfer of low density lipoprotein receptor gene acutely accelerates cholesterol clearance in normal mice," *Proc. Natl. Acad. Sci. USA* 90:2812–2816, 1993.
Hess et al., *J. Adv. Enzyme Reg.,* 7:149, 1968.
Hitzeman et al., *J. Biol. Chem.,* 255:2073, 1980.
Holland et al., *Biochemistry,* 17:4900, 1978.
Holland et al., *Virology,* 101:10–18, 1980.
Honess and Roizman, *J. Virol.,* 14:8–19, 1974.
Honess and Roizman, *J. Virol.,* 16:1308–1326, 1975
Horwich et al., "Synthesis of hepadenovirus particles that contain replication-defective duck hepatitis B virus genomes in cultured HuH7 cells," *J. Virol.,* 64:642–650, 1990.
Innis et al., *PCR™ Protocols,* Academic Press, Inc., San Diego Calif., 1990.
Inouye et al., *Nucleic Acids Res.,* 13: 3101–3109, 1985.
Irwin et al., *J. Virol.,* 68:5036–5044, 1994.
Johnson et al., "Peptide Turn Mimetics" IN: *Biotechnology And Pharmacy,* Pezzuto et al., (eds.), Chapman and Hall, New York, 1993.
Jolly, "Viral vector systems for gene therapy," *Can. Gene Ther.,* 1:51–64, 1994.
Jones and Shenk, "Isolation of deletion and substitution mutants of adenovirus type 5," *Cell,* 13:181–188, 1978.
Jones, *Genetics,* 85: 12, 1977.
Kafri et al., Sustained expression of genes delivered directly into liver and muscle by lentiviral vectors. *Nat. Genet.* 17:314–317, 1997.
Kaneda et al., "Increased expression of DNA cointroduced with nuclear protein in adult rat liver," *Science,* 243:375–378, 1989.
Karlsson et al., *EMBO J.,* 5:2377–2385, 1986.
Kato et al., "Expression of hepatitis β virus surface antigen in adult rat liver," *J. Biol. Chem.,* 266:3361–3364, 1991.
Kearns et al., *Gene Ther.,* 3:748–755, 1996.

Kingsman et al., *Gene*, 7: 141, 1979.

Kitten et al. *Hum. Gene Ther.*, 8:1491–1494, 1997.

Klein et al., "High-velocity microprojectiles for delivering nucleic acids into living cells," *Nature*, 327:70–73, 1987.

Kotin and Berns, *Virol.*, 170:460–467, 1989.

Kotin et al., *Genomics*, 10:831–834, 1991.

Kotin et al., *Proc. Natl. Acad. Sci. USA*, 87:2211–2215, 1990.

Kwoh et al., *Proc. Nat. Acad. Sci. USA*, 86:1173, 1989.

Kyte and Doolittle, "A simple method for displaying the hydropathic character of a protein," *J. Mol. Biol.*, 157(1):105–132, 1982.

Le Gal La Salle et al., "An adenovirus vector for gene transfer into neurons and glia in the brain," *Science*, 259:988–990, 1993.

Levrero et al., *Gene*, 101:195–202, 1991.

Lishanski et al., *Proc. Nat'l. Acad. Sci USA.*, 91:2674–2678, (1994)

Lowy et al., *Cell*, 22: 817, 1980.

Macejak and Sarnow, *Nature*, 353:90–94, 1991.

Mann et al., "Construction of a retrovirus packaging mutant and its use to produce helper-free defective retrovirus," *Cell*, 33:153–159, 1983.

Mann et al., *Cell*, 33:153–159, 1983.

Markowitz et al., "A safe packaging line for gene transfer: Separating viral genes on two different plasmids," *J. Virol.*, 62:1120–1124, 1988.

McCormack et al. *Hum. Gene Ther.* 8: 1263–1273, 1997.

Miller et al., PCT Application WO 89/06700

Miyoshi et al., *Proc. Natl. Acad. Sci. USA* 94:10319–10323.

Mizukami et al., *Virology*, 217:124–130, 1996.

Mulligan et al., *Proc. Nat'l Acad. Sci. USA*, 78: 2072, 1981.

Mulligan, "The basic science of gene therapy," *Science*, 260:926–932, 1993.

Myers, EP 0273085

Naldini et al., *Science* 272:263–267.

Nicolas and Rubenstein, "Retroviral vectors," In: *Vectors: A survey of molecular cloning vectors and their uses*, Rodriguez and Denhardt (eds.), Stoneham: Butterworth, pp. 493–513, 1988.

Nicolas and Rubenstein, In: *Vectors: A survey of molecular cloning vectors and their uses*, Rodriguez and Denhardt (eds.), Stoneham: Butterworth, pp. 493–513, 1988.

Nicolau and Sene, "Liposome-mediated DNA transfer in eukaryotic cells," *Biochim. Biophys. Acta*, 721:185–190, 1982.

Nicolau et al., "Liposomes as carriers for in vivo gene transfer and expression," *Methods Enzymol.*, 149:157–176, 1987.

O'Hare et al., *Proc. Nat'l Acad. Sci. USA*, 78: 1527, 1981.

Ohara et al., *Proc. Nat'l Acad. Sci. USA*, 86: 5673–5677, 1989.

Olsen, J. C., L. G. Johnson, J. M. Stutts, B. Sarkadi, J. R. Yankaskas, R. Swanstrom, and R. C. Boucher. 1992. Correction of the apical membrane chloride permeability defect in polarized cystic fibrosis airway epithelia following retroviral-mediated gene transfer. *Hum. Gene Ther.* 3:253–266.

Olsen, Johnson, Wong-Sun, Moore, Swanstrom, and Boucher, "Retrovirus-mediated gene transfer to cystic fibrosis airway epithelial cells: effect of selectable marker sequences on long-term expression," *Nucleic Acids Res.*, 21(3):663–669, 1993.

Ostrove et al., *Virology*, 113:532–533, 1981.

Paskind et al., "Dependence of moloney murine leukemia virus production on cell growth," *Virology*, 67:242–248, 1975.

Paskind et al., *Virology*, 67:242–248, 1975.

Pelletier and Sonenberg, *Nature*, 334:320–325, 1988.

Perales et al., "Gene transfer in vivo: Sustained expression and regulation of genes introduced into the liver by receptor-targeted uptake," *Proc. Natl. Acad. Sci.* 91:4086–4090, 1994.

Pignon et al., *Hum. Mutat.*, 3: 126–132, 1994.

Poeschla, E. M., F. W-Staal, and D. L. Looney. 1998. Efficient transduction of nondividing human cells by feline immunodeficiency virus lentiviral vectors. *Nature Med.* 4:354–357.

Ponnazhagan et al., *Hum. Gene Ther.*, 8:275–284, 1997a.

Ponnazhagan et al., *J. Gen. Virol.*, 77:1111–1122, 1996.

Post et al., *Cell*, 24:555–565, 1981.

Potter et al., "Enhancer-dependent expression of human k immunoglobulin genes introduced into mouse pre-B lymphocytes by electroporation," *Proc. Nat. Acad. Sci. USA*, 81:7161–7165, 1984.

Racher et al., *Biotechnology Techniques*, 9:169–174, 1995.

Ragot et al., "Efficient adenovirus-mediated transfer of a human minidystrophin gene to skeletal muscle of mdx mice," *Nature*, 361:647–650, 1993.

Renan, "Cancer genes: Current status, future prospects and applications in radiotherapy/oncology," *Radiother. Oncol.*, 19:197–218, 1990.

Renan, *Radiother. Oncol.*, 19:197–218, 1990.

Rich et al., "Development and analysis of recombinant adenoviruses for gene therapy of cystic fibrosis," *Hum. Gene Ther.*, 4:461–476, 1993.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.*, 10:689–695, 1990.

Roizman and Sears, In *Fields' Virology*, 3rd Edition, eds. Fields et al. (Raven Press, New York, N.Y.), pp. 2231–2295, 1995.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemiavirus-derived viruses," *Proc. Natl Acad. Sci. USA*, 86:9079–9083, 1989.

Sambrook et al., *Molecular cloning: A laboratory manual*, 2d Ed., Cold Spring Harbor Laboratory Press, Cold Spring Harbor, N.Y., 1989.

Samulski et al, *EMBO J.*, 10:3941–3950, 1991.

Srivastava et al., *J. Virol.*, 45:555–564, 1983.

Stinchcomb et al., *Nature*, 282: 39, 1979.

Stratford-Perricaudet and Perricaudet, "Gene transfer into animals: the promise of adenovirus," p. 51–61, In: *Human Gene Transfer*, Cohen-Haguenauer and Boiron (eds.), Editions John Libbey Eurotext, France, 1991.

Stratford-Perricaudet et al., "Evaluation of the transfer and expression in mice of an enzyme-encoding gene using a human adenovirus vector," *Hum. Gene. Ther.*, 1:241–256, 1990.

Summers et al. "A manual of methods for baculovirus vectors and insect cell culture procedures," Texas Agriculture Experimental Station.

Szybalska et al., *Proc. Nat'l Acad. Sci. USA*, 48:2026, 1962.

Temin, "Retrovirus vectors for gene transfer: Efficient integration into and expression of exogenous DNA in vertebrate cell genome," In: *Gene Transfer,* Kucherlapati (ed.), New York, Plenum Press, pp. 149–188, 1986.

Temin, *In: Gene Transfer,* Kucherlapati (ed.), New York: Plenum Press, pp. 149–188, 1986.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Tschemper et al., *Gene,* 10: 157, 1980.

Tur-Kaspa et al., "Use of electroporation to introduce biologically active foreign genes into primary rat hepatocytes," *Mol. Cell Biol.,* 6:716–718, 1986.

U.S. Pat. No. 4,683,195

U.S. Pat. No. 4,683,202

U.S. Pat. No. 4,800,159

Varmus et al., "Retroviruses as mutagens: Insertion and excision of a nontransforming provirus alter the expression of a resident transforming provirus," *Cell,* 25:23–36, 1981.

Wagner et al., *Proc. Natl. Acad. Sci.* 87(9):3410–3414, 1990.

Wagner et al., *Science,* 260:1510–1513, 1993.

Walker et al., *Proc. Nat'l Acad. Sci. USA* 89:392–396 1992.

Wigler et al., *Cell,* 11: 223, 1977.

Wigler et al., *Proc. Nat'l Acad. Sci. USA,* 77: 3567, 1980.

Wong et al., "Appearance of β-lactamase activity in animal cells upon liposome mediated gene transfer," *Gene,* 10:87–94, 1980.

Wu and Wu, "Evidence for targeted gene delivery to HepG2 hepatoma cells in vitro," *Biochem.,* 27:887–892, 1988.

Wu and Wu, "Receptor-mediated in vitro gene transfections by a soluble DNA carrier system," *J. Biol. Chem.,* 262:4429–4432, 1987.

Wu and Wu, *Adv. Drug Delivery Rev.,* 12:159–167, 1993.

Wu et al., *Genomics,* 4:560, 1989.

Yang et al., "In vivo and in vitro gene transfer to mammalian somatic cells by particle bombardment," *Proc. Natl. Acad. Sci USA,* 87:9568–9572, 1990.

Zelenin et al., "High-velocity mechanical DNA transfer of the chloramphenicol acetyltransferase gene into rodent liver, kidney and mammary gland cells in organ explants and in vivo," *FEBS Lett.,* 280:94–96, 1991.

What is claimed is:

1. A method of synthesizing a double-stranded polynucleotide, comprising:
   (a) annealing a 5' terminal oligonucleotide with a 3' terminal oligonucleotide of a double-stranded polynucleotide to produce a first annealed product and directly adding a next most terminal oligonucleotide of said double-stranded polynucleotide to said first annealed product under conditions sufficient for annealing to produce a second annealed product, said next most terminal oligonucleotide having a length of at least about 25 bases, and
   (b) repeating step (a) one or more times to sequentially produce a double-stranded polynucleotide.

2. The method of claim 1, further comprising the step of treating said annealed oligonucleotides with a ligating enzyme.

3. The method of claim 1, further comprising the step of amplifying said double-stranded polynucleotide.

4. The method of claim 1, wherein said double-stranded polynucleotide comprises a length selected from the group consisting of 100, 200, 300, 400, 500, 600, 700, 800, 900, 1000, 5000, $10\times10^3$, $20\times10^3$, $30\times10^3$, $40\times10^3$, $50\times10^3$, $60\times10^3$, $70\times10^3$, $80\times10^3$, $90\times10^3$, $1\times10^4$, $1\times10^5$, $1\times10^6$, $1\times10^7$, $1\times10^8$, $1\times10^9$ and $1\times10^{10}$ base pairs.

5. The method of claim 1, wherein said double-stranded polynucleotide comprises a coding region and a corresponding regulatory element directing the expression of said coding region.

6. The method of claim 5, wherein said regulatory element further comprises a promoter.

7. The method of claim 1, wherein said double-stranded polynucleotide further comprises a plurality of coding regions and a plurality of regulatory elements.

8. The method of claim 7, wherein said coding regions encode products that comprise a biochemical pathway.

9. The method of claim 8, wherein said biochemical pathway is glycolysis.

10. The method of claim 9, wherein said coding regions encode enzymes selected from the group consisting of hexokinase, phosphohexose isomerase, phosphofructokinase-1, aldolase, triose-phosphate isomerase, glyceraldehyde-3-phosphate dehydrogenase, phosphoglycerate kinase, phosphoglycerate mutase, enolase and pyruvate kinase.

11. The method of claim 8, wherein said biochemical pathway is lipid synthesis.

12. The method claim 7, wherein said biochemical pathway is cofactor synthesis.

13. The method of claim 7, wherein said pathway involves lipoic acid.

14. The method of claim 7, wherein said biochemical pathway is riboflavin synthesis.

15. The method of claim 7, wherein said biochemical pathway is nucleotide synthesis.

16. The method of claim 15, wherein said nucleotide is a purine.

17. The method of claim 15, wherein said nucleotide is a pyrimidine.

18. The method of claim 7, wherein said coding regions encode enzymes involved in a cellular process selected from the group consisting of cell division, chaperone, detoxification, peptide secretion, energy metabolism, regulatory function, DNA replication, transcription, RNA processing and tRNA modification.

19. The method of claim 18, wherein said energy metabolism is oxidative phosphorylation.

20. The method of claim 1, wherein said double-stranded polynucleotide is a DNA.

21. The method of claim 1, wherein said double-stranded polynucleotide is an RNA.

22. The method of claim 1, wherein said double-stranded polynucleotide is an expression construct.

23. The method of claim 22, wherein said expression construct is a bacterial expression construct.

24. The method of claim 22, wherein said expression construct is a mammalian expression construct.

25. The method of claim 17, wherein said expression construct is a viral expression construct.

26. The method of claim 1, wherein said double-stranded polynucleotide comprises a genome selected from the group consisting of bacterial genome, yeast genome, viral genome, mammalian genome, amphibian genome and avian genome.

27. The method of claim 1, wherein each said overlap is between about 5 base pairs and about 75 base pairs.

28. The method of claim 1, wherein said overlap is selected form the group consisting of about 10 base pairs, about 15 base pairs, about 20 base pairs, about 25 base pairs, about 30 base pairs, about 35 base pairs, about base pairs, about 45 base pairs, about 50 base pairs, about 55 base pairs, about 60 base pairs, about 65 base pairs, and about 70 base pairs.

29. The method of claim 5, wherein said promoter is selected from the group consisting of CMV IE, SV40 IE, RSV, β-actin, tetracycline regulatable and ecdysone regulatable.

30. The method of claim 26, wherein said genome is a viral genome.

31. The method of claim 30, wherein said viral genome is selected from the group consisting of retrovirus, adenovirus, vaccinia virus, herpesvirus and adeno-associated virus.

32. The method of claim 1, wherein said double-stranded polynucleotide is a chromosome.

33. A method of producing a viral particle comprising the steps of:
   (a) providing a host cell;
   (b) transforming said host cell with an artificial viral genome prepared by: (i) generating a first set of oligonucleotides comprising one strand of said viral genome; (ii) generating a second set of oligonucleotides comprising the second complementary strand of said viral genome; and (iii) annealing said first and said second set of oligonucleotides; wherein each of said oligonucleotides of said second set of oligonucleotides overlaps with and hybridizes to two complementary oligonucleotides of said first set of oligonucleotides, except that two oligonucleotides at a 5' or 3' end of said viral genome will hybridize with only one complementary oligonucleotide; and
   (c) culturing said transformed host cell under conditions such that said viral particle is expressed.

34. The method of claim 33, wherein said viral genome is selected from the group consisting of retrovirus, adenovirus, vaccinia virus, herpesvirus and adeno-associated virus.

35. The method of claim 1, wherein said double-stranded polynucleotide comprises an artificial chromosome, wherein said chromosome comprises all coding regions and regulatory elements found in a corresponding natural chromosome.

36. The method of claim 35, wherein said corresponding natural chromosome is a human mitochondrial genome.

37. The method of claim 35, wherein said corresponding natural chromosome is a chloroplast genome.

38. The method of claim 1, wherein said double-stranded polynucleotide comprises an artificial genetic system, wherein said system comprises all coding regions and regulatory elements found in a corresponding natural biochemical pathway.

39. The method of claim 38, wherein said biochemical pathway comprises the activities required for glycolysis.

40. The method of claim 38, wherein said biochemical pathway comprises the enzymes required for electron transport.

41. The method of claim 38, wherein said biochemical pathway comprises the enzyme activities required for photosynthesis.

42. The method of claim 1, wherein said next most terminal oligonucleotide of said double-stranded polynucleotide has an overlap of about 50 percent with said first annealed product.

43. A method of synthesizing a replication-competent double-stranded polynucleotide, comprising:

(a) annealing a 5' terminal oligonucleotide with a 3' terminal oliogonucleotide of a replication-competent double-stranded polynucleotide to produce a first annealed product and directly adding a next most terminal oligonucleotide of said replication-competent double-stranded polynucleotide to said first annealed product under conditions sufficient for annealing to produce a second annealed product, and (b) repeating step (a) one or more times to sequentially produce a replication-competent double-stranded polynucleotide.

44. A method of synthesizing a double-stranded polynucleotide, comprising:

(a) annealing a 5' terminal oligonucleotide with a 3' terminal oliogonucleotide of a double-stranded polynucleotide to produce a first annealed product and directly adding a next most terminal double-stranded polynucleotide to said first annealed product under conditions sufficient for annealing to produce a second annealed product, said next most terminal double-stranded polynucleotide comprising at least one oligonucleotide of at least about 25 bases, and (b) repeating step (a) one or more times to sequentially produce a double-stranded polynucleotide.

45. A method of synthesizing a replication-competent double-stranded polynucleotide, comprising:

(a) annealing a 5' terminal oligonucleotide with a 3' terminal oliogonucleotide of a replication-competent double-stranded polynucleotide to produce a first annealed product and directly adding a next most terminal double-stranded polynucleotide to said first annealed product under conditions sufficient for annealing to produce a second annealed product, and (b) repeating step (a) one or more times to sequentially produce a replication-competent double-stranded polynucleotide.

* * * * *

UNITED STATES PATENT AND TRADEMARK OFFICE
CERTIFICATE OF CORRECTION

PATENT NO. : 6,521,427 B1
DATED : February 18, 2003
INVENTOR(S) : Evans

It is certified that error appears in the above-identified patent and that said Letters Patent is hereby corrected as shown below:

<u>Column 101,</u>
Line 48, please delete "method" and replace with -- method of --.

<u>Column 102,</u>
Line 19, please delete "form" and replace with -- from --.
Line 21, please delete "about base" and replace with -- about 40 base --.

Signed and Sealed this

Third Day of February, 2004

JON W. DUDAS
*Acting Director of the United States Patent and Trademark Office*